United States Patent
Deshmukh et al.

(10) Patent No.: US 9,278,330 B2
(45) Date of Patent: Mar. 8, 2016

(54) MICROCHANNEL APPARATUS COMPRISING STRUCTURED WALLS, CHEMICAL PROCESSES, METHODS OF MAKING FORMALDEHYDE

(75) Inventors: Soumitra Deshmukh, Dublin, OH (US); Anna Lee Tonkovich, Dublin, OH (US); Terry Mazanec, Solon, OH (US); Bin Yang, Columbus, OH (US); Kai Jarosch, Bexley, OH (US); Richard Long, New Albany, OH (US)

(73) Assignee: Velocys, Inc., Plain City, OH (US)

( * ) Notice: Subject to any disclaimer, the term of this patent is extended or adjusted under 35 U.S.C. 154(b) by 264 days.

(21) Appl. No.: 12/825,303

(22) Filed: Jun. 28, 2010

(65) Prior Publication Data

US 2010/0267993 A1     Oct. 21, 2010

Related U.S. Application Data

(62) Division of application No. 12/099,142, filed on Apr. 7, 2008, now Pat. No. 7,745,667.

(51) Int. Cl.
| | |
|---|---|
| *B01J 8/06* | (2006.01) |
| *B01J 19/00* | (2006.01) |
| *B01J 23/28* | (2006.01) |
| *B01J 23/887* | (2006.01) |
| *B01J 37/02* | (2006.01) |
| *C07C 45/38* | (2006.01) |
| *B01J 21/06* | (2006.01) |
| *B01J 29/03* | (2006.01) |

(52) U.S. Cl.
CPC .............. *B01J 19/0093* (2013.01); *B01J 23/28* (2013.01); *B01J 23/8877* (2013.01); *B01J 37/0203* (2013.01); *B01J 37/0205* (2013.01); *B01J 37/0225* (2013.01); *B01J 37/0244* (2013.01); *B01J 37/0248* (2013.01); *C07C 45/38* (2013.01); *B01J 21/063* (2013.01); *B01J 29/0308* (2013.01); *B01J 2219/0086* (2013.01); *B01J 2219/00822* (2013.01); *B01J 2219/00835* (2013.01); *B01J 2219/00844* (2013.01); *B01J 2219/00873* (2013.01); *B01J 2219/00889* (2013.01); *B01J 2219/00984* (2013.01); *B01J 2229/18* (2013.01)

(58) Field of Classification Search
CPC .................................... B01J 8/06; B01J 8/008
USPC .......................................... 422/653, 652, 312
See application file for complete search history.

(56) References Cited

U.S. PATENT DOCUMENTS

| | | |
|---|---|---|
| 4,739,124 A | 4/1988 | Ward |
| 4,760,210 A | 7/1988 | Sweeney |
| 5,405,586 A | 4/1995 | Koves |
| 5,609,834 A | 3/1997 | Hamada et al. |
| 5,700,434 A | 12/1997 | Gaiser |
| 5,811,062 A | 9/1998 | Wegeng et al. |
| 5,997,826 A * | 12/1999 | Lodeng et al. ............... 422/634 |
| 6,117,578 A | 9/2000 | Lesieur |
| 6,118,038 A | 9/2000 | Lankton et al. |
| 6,159,358 A | 12/2000 | Mulvaney et al. |
| 6,159,434 A | 12/2000 | Gonjo et al. |
| 6,166,283 A | 12/2000 | Bharadwaj |
| 6,168,765 B1 | 1/2001 | Romatier et al. |
| 6,180,846 B1 | 1/2001 | Dandekar et al. |
| 6,187,273 B1 | 2/2001 | Gaiser |
| 6,190,624 B1 | 2/2001 | Romatier |
| 6,228,341 B1 | 5/2001 | Hebert et al. |
| 6,245,708 B1 | 6/2001 | Wachs et al. |
| 6,274,101 B1 | 8/2001 | Sechrist |
| 6,294,138 B1 | 9/2001 | von Hippel et al. |
| 6,350,918 B2 | 2/2002 | Wachs et al. |
| 6,365,543 B1 | 4/2002 | Schmidt et al. |
| 6,488,838 B1 | 12/2002 | Tonkovich et al. |
| 6,515,146 B1 | 2/2003 | Perregaard et al. |
| 6,518,463 B2 | 2/2003 | Wachs et al. |
| 6,559,345 B2 | 5/2003 | Wachs et al. |
| 6,566,573 B1 | 5/2003 | Bharadwaj |
| 6,709,640 B1 | 3/2004 | Romatier et al. |
| 6,828,143 B1 * | 12/2004 | Bard ............................... 506/15 |
| 6,930,072 B2 | 8/2005 | Wachs et al. |
| 7,193,117 B2 | 3/2007 | Wachs et al. |
| 7,294,734 B2 | 11/2007 | Brophy et al. |
| 2003/0007904 A1 | 1/2003 | Tonkovich et al. |
| 2003/0068261 A1 | 4/2003 | Taheri et al. |
| 2004/0032037 A1 | 2/2004 | Katinger et al. |
| 2004/0034266 A1 | 2/2004 | Brophy et al. |
| 2004/0082804 A1 | 4/2004 | Brophy et al. |
| 2004/0105813 A1 | 6/2004 | Bussche et al. |
| 2004/0125689 A1 | 7/2004 | Ehrfeld et al. |
| 2004/0199039 A1 | 10/2004 | Brophy et al. |
| 2004/0220434 A1 | 11/2004 | Brophy et al. |
| 2004/0229752 A1 * | 11/2004 | Long et al. ................. 502/303 |
| 2005/0048333 A1 | 3/2005 | Pettit |
| 2005/0256358 A1 | 11/2005 | Wang et al. |
| 2006/0292434 A1 * | 12/2006 | Hampden-Smith et al. .... 429/40 |
| 2007/0017633 A1 | 1/2007 | Tonkovich |
| 2007/0256736 A1 | 11/2007 | Tonkovich |

OTHER PUBLICATIONS

Woerz, "Microreactors as Tools in Chemical Research", in Microreaction Technology: Imret 5: Proceedings of the Fifth International Conference on Microreaction Technology, Eds. Michael Matlosz, Wolfgang Ehrfeld, Jorg Peter Baselt, Springer-Verlag Berlin Heidelberg New York, 2002. ISBN: 3-540-41448-7.

Steinfeldt, N. et al. "Comparative Studies of the Oxidative Dehydrogenation of Propane in Micro-Channels Reactor", Module and Fixed-Bed Reactor, in Studies in Surface Science and Atalysis: Eds. J.J. Spivey, E. Iglesia and T.H. Fleisch, Elsevier Science B. V., 2001.

* cited by examiner

*Primary Examiner* — Natalia Levkovich
(74) *Attorney, Agent, or Firm* — Frank Rosenberg

(57) ABSTRACT

Methods for controlling series or series-parallel reactions are described. Novel microchannel apparatus having mesoporous structures adjacent to bulk flow paths are described. Methods of synthesizing formaldehyde from methanol are also described.

10 Claims, 11 Drawing Sheets

MICROCHANNEL APPARATUS COMPRISING STRUCTURED WALLS, CHEMICAL PROCESSES, METHODS OF MAKING FORMALDEHYDE

RELATED APPLICATIONS

This application is a divisional of Ser. No. 12/099,142 filed Apr. 7, 2008, now U.S. Patent No., incorporated herein by reference as if reproduced in full below

INTRODUCTION

Fe—Mo—Ox catalysts are commercially used for the selective oxidation of methanol to formaldehyde. The reaction is conducted in a multi-tubular reactor with a circulating heat-transfer fluid in the shell. The reaction temperature is 350-450° C. However, since the reaction is exothermic, hot spots occur in the catalyst bed. Such "hot spots" promote the sublimation of Mo as "molybdenum blue" which in turn leads to the catalyst deactivation. Consequently, Fe—Mo oxide catalysts need to be replaced in every 6-12 months.

Conducting chemical processes in microchannels is well known to be advantageous for enhanced heat and mass transfer.

SUMMARY OF THE INVENTION

The invention provides methods of conducting series or series-parallel reactions. The invention further provides novel microchannel devices and methods of conducting reactions in microchannel devices. The invention also provides improved methods of making formaldehyde and catalysts useful for making formaldehyde.

In a first aspect, the invention provides a method of conducting a series or series-parallel reaction, comprising: passing a first reactant into a microchannel; passing a second reactant into the microchannel in plural stages; wherein the first and second reactant react in each stage; wherein the yield of primary product from the method, based on the first reactant, is at least 90%, and wherein, at the end of each stage, the second reactant is not completely consumed but is present in a range of 0.01 to 10 mol %. In some embodiments, the second reactant is staged according to a non-linear decreasing profile of successive stage feed amounts. In some embodiments, the method comprises a multiphase reaction; for example, a three phase (gas-liquid-solid) reaction (e.g. hydrogenation of fatty acids on Ni catalyst). In another preferred multiphase reaction, the first reactant comprises a liquid and the liquid is fed through into the microchannel through an inlet, the second reactant comprises a gas that is fed through apertures into the microchannel, and the first reactant and the second reactant react at a solid catalyst loaded on to a microchannel wall. In another preferred embodiment of this method, 2 or more reactants are fed through a main microchannel and one or more of these reactants are fed into the microchannel through apertures in a plurality of stages. In a preferred embodiment, the first reactant is methanol and the second reactant is oxygen (formaldehyde can be synthesized in this method). In a preferred method of synthesizing formaldehyde, the methanol and oxygen react over a catalyst comprising a mixture of vanadium and molybdenum oxides disposed on titania disposed on a mesoporous matrix. In another embodiment of this method, a catalyst is disposed on a mesoporous matrix and the mesoporous matrix is disposed in wells along the length of the microchannel (preferably, there is a bulk flow path in the microchannel that is adjacent to the catalyst on the mesoporous matrix; preferably, the walls of the wells are tapered. In some embodiments, a portion of the second reactant is combined with the first reactant prior to entering the microchannel.

In a second aspect, the invention provides a method of conducting a series or series-parallel reaction, comprising: passing a stream comprising a first reactant into a bulk flow path having at least one dimension of 2 mm or less; wherein, adjacent to the bulk flow path, there is a catalyst supported on a mesoporous matrix; wherein the first reactant reacts with a second reactant on the catalyst that is supported on a mesoporous matrix; wherein the volume occupied by the catalyst supported on a mesoporous matrix plus the volume of bulk flow path that is adjacent to the catalyst supported on a mesoporous matrix defines the volume of reaction chamber; and controlling the flow of reactants such that at least 90% of the stream has a residence time in the reaction chamber that varies by less than 10% of the mass average residence time. In some preferred embodiments, the method is further characterized by one or any combination of the following: yield of a single product is at least 90% based on mass of first reactant; the first reactant is MeOH and the second is $O_2$; the second reactant is added through apertures along the length of the bulk flow path; the second reactant is added through apertures behind the mesoporous matrix (that is, the mesoporous matrix is disposed between apertures and a bulk flow path; temperature in the catalyst is at least 250° C.; the mesoporous matrix is disposed in recesses having sloped walls; and/or $O_2$ content is controlled to never exceed 10 molar %.

Any of the inventive methods can be further characterized by any of the conditions or reaction properties described in the Detailed Description section; for example, specified average residence time, residence time distribution, contact times, yields and relative amounts of reactants. The inventive methods can also be characterized by any of the apparatus features described herein, optionally including a step of providing microchannel apparatus having specified features. Likewise, any of the inventive apparatus can be further characterized by any of the any of structural features described in the Detailed Description section.

In a further aspect, the invention provides microchannel apparatus, comprising: a bulk flow path 101 having at least one dimension of 2 mm or less; a channel wall adjacent to the bulk flow path; wherein the channel wall 102 comprises a well 103 with sloped walls 104 and a mesoporous matrix material 105 disposed in the well; and wherein the mesoporous matrix 105 is confined in the well and does not coat walls of the bulk flow path outside the well. In some embodiments, in addition to the catalyst on the mesporous matrix, there is also a catalyst (not mesoporous) 107 disposed on walls around the bulk flow path that is not within a well; this would commonly occur in cases where catalyst is applied insitu into a reaction microchannel. In some preferred embodiments, the apparatus has one or any combination of the following features: mesoporous matrix is a structured wall; a structured wall is made of layers forming a stair-step design; specific dimensions of well and stairs as described herein; the slope of the well's walls are substantially straight (slope of a tapered well wall is in the preferably in the range of 30-60 degrees); well is over the entire width of the microchannel (length is flow direction 106 through bulk flow path, height is the stacking direction in a laminated device; length, height and width are mutually perpendicular); bulk flow path is rectangular, cylindrical or triangular. Of course, the apparatus is not limited to such features, for example, apparatus could have any of the features described elsewhere in this specification.

The invention also includes methods of conducting unit operations in any of the apparatus described herein. For example, in another aspect, the invention provides a method of conducting a unit operation in microchannel apparatus as described herein, comprising: passing a fluid into the bulk flow path; wherein the fluid flows in a direction through the bulk flow path, and wherein the well has a leading edge and a trailing edge and the leading edge of the well slopes down and the trailing edge slopes up; and conducting a unit operation on the fluid as it passes through the microchannel apparatus.

In a further aspect, the invention provides microchannel apparatus, comprising: a bulk flow path; a structured wall adjacent to the bulk flow path; wherein during operation of the apparatus there is a direction of fluid flow through the bulk flow path; wherein the structured wall comprises crossbars in the top most layer of the structured wall having angles of from 10° to 80° with respect to the direction of flow; and further wherein the structured wall comprises a subsurface layer having apertures and crossbars, wherein the crossbars in the subsurface layer have angles, with respect to the direction of flow through the bulk flow path, that are different than the angles in the top-most layer; and wherein the top-most layer and the subsurface layers have leading edges where, viewed in the direction of flow, apertures first appear in each layer, and wherein the leading edge of the subsurface layer has a tapered shape that corresponds to the angle of cross-bars in the top-most layer so that fluids from the bulk flow path are not trapped beneath the top-most layer. An example of such apparatus is illustrated in FIG. 14. In one preferred embodiment, the subsurface layer is oriented as a mirror-image of the top layer; optionally, several such top layer and subsurface layer combinations may be used to form the structured wall;

The invention also includes microchannel systems comprising a device and a fluid, comprising any of the apparatus described herein in conjunction with one or more fluids passing through the device.

The invention further provides a method of synthesizing formaldehyde in microchannel apparatus, comprising: passing methanol into a channel; wherein the channel comprises a bulk flow path, a formaldehyde synthesis catalyst supported on a mesoporous matrix adjacent to the bulk flow path, and channel walls comprising plural apertures; passing oxygen through the plural apertures; wherein the methanol and the oxygen react on the formaldehyde synthesis catalyst; wherein the oxygen content is controlled such that the molar % of oxygen does not exceed 10% in any 5 volume % of the channel and wherein the amount (molar) of methanol exceeds the amount of oxygen in any 5 volume % of the channel (where the 5% volume is based a continuous length and covers an entire cross-sectional area over the continuous length); and producing a product stream comprising formaldehyde in a yield of at least 90% based on the methanol reactant.

For any of the methods discussed herein, in some embodiments, the method can be conducted at a contact time of 1 ms or less. In some embodiments, temperature or catalyst activity of concentration can be varied along the length of the reaction channel.

In another aspect, the invention provides a method of synthesizing formaldehyde in microchannel apparatus, comprising: passing methanol into a channel; wherein the channel comprises a bulk flow path, a formaldehyde synthesis catalyst supported on a mesoporous matrix adjacent to the bulk flow path, and channel walls comprising plural apertures; passing oxygen through the plural apertures; wherein the methanol and the oxygen react on the formaldehyde synthesis catalyst; wherein the oxygen content is controlled such that the concentration of oxygen entering any stage of the microchannel apparatus is greater than 1 mol %; and producing a product stream comprising formaldehyde in a yield of at least 90% based on the methanol reactant.

In another aspect, the invention provides a method of synthesizing formaldehyde in microchannel apparatus, comprising: passing methanol into a channel; wherein the channel comprises a bulk flow path, a formaldehyde synthesis catalyst supported on a mesoporous matrix adjacent to the bulk flow path, and channel walls comprising plural apertures; passing oxygen through the plural apertures; wherein the oxygen content is controlled such that the concentration of oxygen entering a stage of the microchannel apparatus is greater than 1 molar %; wherein the methanol and the oxygen react on the formaldehyde synthesis catalyst; wherein the oxygen content is controlled such that the concentration of oxygen exiting any stage of the microchannel apparatus is greater than 0.01% by mole (in some embodiments 0.05 mol %); and producing a product stream comprising formaldehyde in a yield of at least 90% based on the methanol reactant. In some preferred embodiments, the concentration of oxygen entering each stage of the microchannel apparatus is greater than 1 molar %

In a further aspect, the invention provides a method of synthesizing formaldehyde in microchannel apparatus, comprising: passing methanol into a channel; wherein the channel comprises a bulk flow path, a formaldehyde synthesis catalyst supported on a mesoporous matrix adjacent to the bulk flow path, and channel walls comprising plural apertures; passing oxygen through the plural apertures; wherein the methanol and the oxygen react on the formaldehyde synthesis catalyst; wherein the plural apertures are spaced an uneven intervals; and producing a product stream comprising formaldehyde in a yield of at least 90% based on the methanol reactant.

In another aspect, the invention provides a method of synthesizing formaldehyde in microchannel apparatus, comprising: passing methanol into a channel; wherein the channel comprises a bulk flow path, a formaldehyde synthesis catalyst supported on a mesoporous matrix adjacent to the bulk flow path, and channel walls comprising plural apertures; passing oxygen through the plural apertures into at least a first stage and a second stage; wherein the methanol and the oxygen react on the formaldehyde synthesis catalyst in each of the first and second stages; wherein the oxygen content is controlled such that the molar % of oxygen does not exceed 10% in each of the first and second stages; and producing a product stream comprising formaldehyde in a yield of at least 90% based on the methanol reactant.

In yet another aspect, the invention provides a method of synthesizing formaldehyde, comprising: passing methanol and oxygen over a catalyst at a temperature of 250° C. or more; wherein the catalyst comprises a mixed V, Mo oxide on a titania support disposed on a mesoporous matrix. One preferred mesoporous matrix is SBA-15, another preferred matrix is a structured wall. Supported $V_2O_5+MoO_3$ catalysts are highly active and selective for formaldehyde production at low temperatures (≤260° C.). Such catalysts are also more resistant to $MoO_3$ sublimation and, hence, more stable than a commercial Fe—Mo catalyst.

In some preferred methods of synthesizing formaldehyde, the method can be further characterized by one or more of the following: the product stream has a temperature of 250° C. or more; the $O_2$ content in the product stream (of any stage, or every stage, or the final stage) is at least 0.01% (volume %); the formaldehyde synthesis catalyst comprises an oxide comprising V, Mo and Ti; a narrow residence time distribution for methanol.

GLOSSARY

Structural features related to manifolding are as defined in U.S. Published Patent Application No. 20050087767, filed Oct. 27, 2003, now U.S. Pat. No. 7,422,910, and U.S. patent application Ser. No. 11/400,056, filed Apr. 11, 2006. Surface features, structured walls, and general device construction can be as described in U.S. Published Patent Applications 20070256736 and 20070017633. All of these patent applications are incorporated herein by reference as if reproduced in full below. In cases where the definitions set forth here are in conflict with definitions in the patent applications referred to above, then the definitions set forth here are controlling.

As is standard patent terminology, "comprising" means "including" and neither of these terms exclude the presence of additional or plural components. For example, where a device comprises a lamina, a sheet, etc., it should be understood that the inventive device may include multiple laminae, sheets, etc. In alternative embodiments, the term "comprising" can be replaced by the more restrictive phrases "consisting essentially of" or "consisting of."

Channels are defined by channel walls that may be continuous or may contain gaps. Interconnecting pathways through a foam or felt are not connecting channels (although a foam, etc. may be disposed within a channel).

"Connecting channels" are channels connected to a manifold. Typically, unit operations occur in connecting channels. Connecting channels have an entrance cross-sectional plane and an exit cross-sectional plane. Although some unit operations or portions of unit operations may occur in a manifold, in preferred embodiments, greater than 70% (in some embodiments at least 95%) of a unit operation occurs in connecting channels. A "connecting channel matrix" is a group of adjacent, substantially parallel connecting channels. In preferred embodiments, the connecting channel walls are straight. In some preferred embodiments, connecting channels are straight with substantially no variation in direction or width. The connecting channel pressure drop for a system of multiple connecting channels is the arithmetic mean of each individual connecting channel pressure drop. That is, the sum of the pressure drops through each channel divided by the number of channels. "Connecting microchannels" have a minimum dimension of 2 mm or less, more preferably 0.5 to 1.5 mm, still more preferably 0.7 to 1.2 mm, and a length of at least 1 cm.

A "header" is a manifold arranged to deliver fluid to connecting channels.

A "height" is a direction perpendicular to length. In a laminated device, height is the stacking direction.

A "hydraulic diameter" of a channel is defined as four times the cross-sectional area of the channel divided by the length of the channel's wetted perimeter.

An "L-manifold" describes a manifold design where flow direction into one manifold is normal to axes of the connecting channel, while the flow direction in the opposite manifold is parallel with the axes of the connecting channels: For example, a header L-manifold has a manifold flow normal to the axes of the connecting channels, while the footer manifold flow travels in the direction of connecting channels axes out of the device. The flow makes an "L" turn from the manifold inlet, through the connecting channels, and out of the device. When two L-manifolds are brought together to serve a connecting channel matrix, where the header has inlets on both ends of the manifold or a footer has exits from both ends of the manifold, the manifold is called a "T-manifold".

A "laminated device" is a device made from laminae that is capable of performing a unit operation on a process stream that flows through the device.

A "length" refers to the distance in the direction of a channel's (or manifold's) axis, which is in the direction of flow.

"M2M manifold" is defined as a macro-to-micro manifold, that is, a microchannel manifold that distributes flow to or from one or more connecting microchannels. The M2M manifold in turn takes flow to or from another larger cross-sectional area delivery source, also known as macro manifold. The macro manifold can be, for example, a pipe, a duct or an open reservoir.

A "manifold" is a volume that distributes flow to two or more connecting channels. The entrance, or inlet, surface of a header manifold is defined as the surface in which marks a significant difference in header manifold geometry from the upstream channel. The exit, or outlet, surface of the footer manifold is defined as the surface which marks a significant difference in the footer manifold channel from the downstream channel. For rectangular channels and most other typical manifold geometries, the surface will be a plane; however, in some special cases such as hemicircles at the interface between the manifold and connecting channels it will be a curved surface.

Manifolds can be L, U or Z types. In a "U-manifold," fluid in a header and footer flow in opposite directions while being at a non zero angle to the axes of the connecting channels.

A "microchannel" is a channel having at least one internal dimension (wall-to-wall, not counting catalyst) of 10 mm or less (preferably 2.0 mm or less) and greater than 1 µm (preferably greater than 10 µm), and in some embodiments 50 to 500 µm; preferably a microchannel remains within these dimensions for a length of at least 1 cm, preferably at least 20 cm. Microchannels are also defined by the presence of at least one inlet that is distinct from at least one outlet. Microchannels are not merely channels through zeolites or mesoporous materials. The length of a microchannel corresponds to the direction of flow through the microchannel. Microchannel height and width are substantially perpendicular to the direction of flow of through the channel. In the case of a laminated device where a microchannel has two major surfaces (for example, surfaces formed by stacked and bonded sheets), the height is the distance from major surface to major surface and width is perpendicular to height.

The value of the Reynolds number describes the flow regime of the stream. While the dependence of the regime on Reynolds number is a function of channel cross-section shape and size, the following ranges are typically used for channels:
Laminar: Re<2000 to 2200
Transition: 2000-2200<Re<4000 to 5000
Turbulent: Re>4000 to 5000.

A large pore support has a porosity of at least 5%, more preferably 30 to 99%, and still more preferably 70 to 98%. Examples of preferred large pore supports include commercially available metal foams and metal felts. Also included are porous layers formed in situ within microchannels such as those formed by chemical templating agents. Preferably, the support has a volumetric average pore size, as measured by BET, of 0.1 µm or greater, more preferably between 1 and 500 µm. Preferred forms of porous supports are foams and felts and these are preferably made of a thermally stable and conductive material, preferably a metal such as stainless steel, inconel, aluminum, silver, or copper or FeCrAlY alloy. These porous supports can be thin, such as between 0.1 and 1 mm. Foams are continuous structures with continuous walls defining pores throughout the structure. Felts are nonwoven fibers with interstitial spaces between fibers and includes tangled strands like steel wool. The porous supports may be stacked between a heat transfer wall and a sheet with apertures. Alternatively, the porous supports may be etched, cut or otherwise have active surface feature grooves placed within the sheets. The sheets may be stacked with non-porous sheets that serve as walls to form an assembly. An active catalyst layer or layers may be disposed upon the large pore support. A catalyst with a large pores (and including the alumina-supported catalytically active sites) preferably has a pore volume of 5 to 98%, more preferably 30 to 95% of the total porous material's volume. Preferably, at least 20% (more preferably at least 50%) of the material's pore volume is composed of pores in the size (diameter) range of 0.1 to 300 microns ($\mu$m), more preferably 0.3 to 200 microns, and still more preferably 1 to 100 microns. Pore volume and pore size distribution are measured by mercury porosimetry (assuming cylindrical geometry of the pores) and nitrogen adsorption. As is known, mercury porosimetry and nitrogen adsorption are complementary techniques with mercury porosimetry being more accurate for measuring large pore sizes (larger than 30 nm) and nitrogen adsorption more accurate for small pores (less than 50 mm). A catalyst, such as a catalyst metal disposed on an oxide layer can be deposited on the large pore support.

A "bulk flow path" refers an open channel within microchannel apparatus that allows rapid gas flow through the reaction chamber without large pressure drops. Bulk flow paths preferably have a cross-sectional area of $5 \cdot 10^{-8}$ to $1 \cdot 10^{-2}$ m$^2$, more preferably $5 \cdot 10^{-7}$ to $1 \cdot 10^{-4}$ m$^2$.

A defined in this invention, a "mesoporous matrix" comprises a "large pore support" or a "structured wall." In some preferred embodiments, the mesoporous matrix comprises a catalytically active surface (such as, but not limited to, a metal oxide supported metal). The mesoporous matrix is on one or more sides of a bulk flow path, or in the case of a curved wall, on at least a portion of the perimeter of the flow path. In preferred embodiments, the mesoporous matrix is in a well. A "well" is a depression within a microchannel wall, and preferably has a depth of 2 mm or less. As described in greater detail herein, a well preferably has sloped walls (most preferably the walls are sloped in the direction of fluid flow though an adjoining bulk flow path) rather than walls that are perpendicular to the bulk flow path.

A "structured wall" refers to a wall that is made up of plural layers in which each of the plural layers have overlapping apertures. The apertures in a layer comprise an open area of at least 0.01 square micrometers ($\mu$m$^2$), preferably 0.01 to 100,000 square micrometers ($\mu$m$^2$), more preferably 5 to 10,000 square micrometers ($\mu$m$^2$); and for a structured wall, each layer must contain at least 10 such apertures, more preferably at least 1000, although there may be intervening layers with less than 10 very large apertures. The apertures should assist in mixing without creating a large dispersion in residence time. A structured wall is on the side of a bulk flow path. Some examples of structured walls are illustrated by Tonkovich et al. in U.S. Published Patent Application Nos. 2007/0256736 and 20060120213, which are incorporated herein by reference.

A "subchannel" is a channel that is within a larger channel. Channels and subchannels are defined along their length by channel walls.

A "sub-manifold" is a manifold that operates in conjunction with at least one other submanifold to make one large manifold in a plane. Sub-manifolds are separated from each other by continuous walls.

A "surface feature" is a projection from, or a recess into, a microchannel wall that modify flow within the microchannel. If the area at the top of the features is the same or exceeds the area at the base of the feature, then the feature may be considered recessed. If the area at the base of the feature exceeds the area at the top of the feature, then it may be considered protruded (except for CRFs discussed below). The surface features have a depth, a width, and a length for non-circular surface features. Surface features may include circles, oblong shapes, squares, rectangles, checks, chevrons, zig-zags, and the like, recessed into the wall of a main channel. The features increase surface area and create convective flow that brings fluids to a microchannel wall through advection rather than diffusion. Flow patterns may swirl, rotate, tumble and have other regular, irregular and or chaotic patterns—although the flow pattern is not required to be chaotic and in some cases may appear quite regular. The flow patterns are stable with time, although they may also undergo secondary transient rotations. The surface features are preferably at oblique angles—neither parallel nor perpendicular to the direction of net flow past a surface. Surface features may be orthogonal, that is at a 90 degree angle, to the direction of flow, but are preferably angled. The active surface features are further preferably defined by more than one angle along the width of the microchannel at least at one axial location. The two or more sides of the surface features may be physically connected or disconnected. The one or more angles along the width of the microchannel act to preferentially push and pull the fluid out of the straight laminar streamlines. Preferred ranges for surface feature depth are less than 2 mm, more preferrably less than 1 mm, and in some embodiments from 0.01 mm to 0.5 mm. A preferred range for the lateral width of the surface feature is sufficient to nearly span the microchannel width (as shown in the herringbone designs), but in some embodiments (such as the fill features) can span 60% or less, and in some embodiments 40% or less, and in some embodiments, about 10% to about 50% of the microchannel width. In preferred embodiments, at least one angle of the surface feature pattern is oriented at an angle of 10°, preferably 30°, or more with respect to microchannel width (90° is parallel to length direction and 0° is parallel to width direction). Lateral width is measured in the same direction as microchannel width. The lateral width of the surface feature is preferably 0.05 mm to 100 cm, in some embodiments in the range of 0.5 mm to 5 cm, and in some embodiments 1 to 2 cm. Some examples of structured walls are illustrated by Tonkovich et al. in U.S. Published Patent Application No. 20070017633, which is incorporated herein by reference.

For staged apparatus with 30 or less apertures (that is, openings for a second reactant), each stage begins at the center point of one aperture to the center point of the next aperture down the length of the reaction channel, and, in the case of the final aperture, the stage length is the channel's outlet. For apparatus with continuous staging (such as through a porous membrane or any configuration with more than 30 apertures for the second reactant) into a reaction channel, the apparatus is considered to have 10 stages of each length beginning at the start of the first aperture and ending at the outlet or the area of the channel that has a sufficiently low temperature such that negligible primary reaction is occurring.

"Unit operation" means chemical reaction, vaporization, compression, chemical separation, distillation, condensation, mixing, heating, or cooling. A "unit operation" does not mean merely fluid transport, although transport frequently occurs along with unit operations. In some preferred embodiments, a unit operation is not merely mixing.

The volume of a connecting channel or manifold is based on open space. The volume includes depressions of surface features. The volume of gate or grate features (which help equalize flow distribution as described in the incorporated published patent application) are included in the volume of manifold; this is an exception to the rule that the dividing line between the manifold and the connecting channels is marked by a significant change in direction. Channel walls are not included in the volume calculation. Similarly, the volume of orifices (which is typically negligible) and flow straighteners (if present) are included in the volume of manifold.

In a "Z-manifold," fluid in a header and footer flow in the same direction while being at a non zero angle to the axes of the connecting channels. Fluid entering the manifold system exits from the opposite side of the device from where it enters. The flow essentially makes a "Z" direction from inlet to outlet.

DETAILED DESCRIPTION OF THE INVENTION

Microchannel Apparatus

Figure 1:
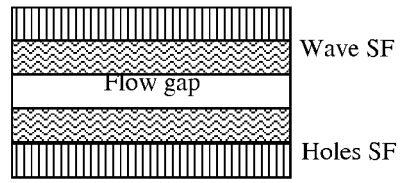
FIG. 1 shows a cross-sectional schematic view of the type of microchannel reactor used in the examples. Directly adjacent to the bulk flow path is a shim with wave-shaped surface features and the top and bottom shims have holes to allow for the passage of a fluid.
Figure 2:
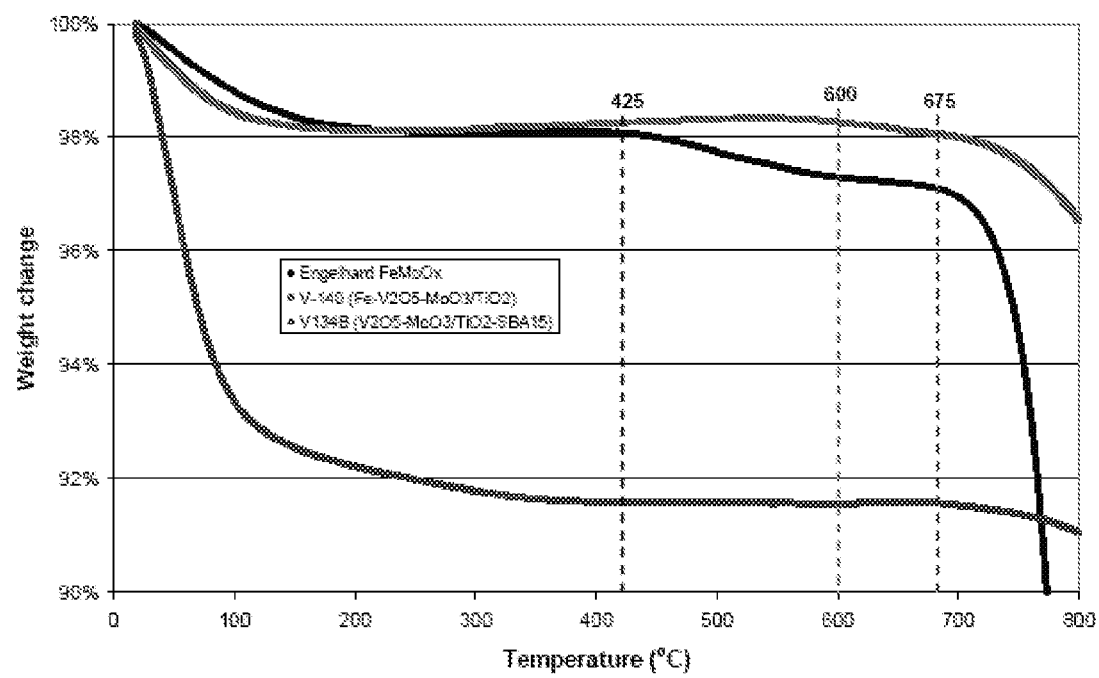
FIG. 2 shows thermal gravimetric analysis (TGA) showing the weight change (loss of $MoO_3$) as a function of temperature of three formaldehyde catalysts: $Fe(V_2O_5)$—$MoO_3$ on $TiO_2$ (top line at 600° C.), FeMoOx (obtained from Engelhard); and $V_2O_5$—$MoO_3$ on $TiO_2$/SBA-15 (bottom line at 600° C.).

Microchannel reactors are characterized by the presence of at least one reaction channel having at least one dimension (wall-to-wall, not counting catalyst) of 1 cm or less, preferably 2 mm or less (in some embodiments about 1.0 mm or less) and greater than 1 µm, and in some embodiments 50 to 500 µm. A catalytic reaction channel is a channel containing a catalyst, where the catalyst may be heterogeneous or homogeneous. A homogeneous catalyst may be co-flowing with the reactants. Microchannel apparatus is similarly characterized, except that a catalyst-containing reaction channel is not required. The gap (or height) of a microchannel is preferably about 2 mm or less, and more preferably 1 mm or less. The length of a reaction channel is typically longer. Preferably, the length is greater than 1 cm, in some embodiments greater than 50 cm, in some embodiments greater than 20 cm, and in some embodiments in the range of 1 to 100 cm. The sides of a microchannel are defined by reaction channel walls. These walls are preferably made of a hard material such as a ceramic, an iron based alloy such as steel, or a Ni-, Co- or Fe-based superalloy such as monel. They also may be made from plastic, glass, or other metal such as copper, aluminum and the like. The choice of material for the walls of the reaction channel may depend on the reaction for which the reactor is intended. In some embodiments, reaction chamber walls are comprised of a stainless steel or Inconel® which is durable and has good thermal conductivity. The alloys should be low in sulfur, and in some embodiments are subjected to a desulfurization treatment prior to formation of an aluminide. Typically, reaction channel walls are formed of the material that provides the primary structural support for the microchannel apparatus. Microchannel apparatus can be made by known methods, and in some preferred embodiments are made by laminating interleaved plates (also known as "shims"), and preferably where shims designed for reaction channels are interleaved with shims designed for heat exchange. Some microchannel apparatus includes at least 10 layers laminated in a device, where each of these layers contain at least 10 channels; the device may contain other layers with less channels.

Microchannel apparatus (such as microchannel reactors) preferably include microchannels (such as a plurality of microchannel reaction channels) and a plurality of adjacent heat exchange microchannels. The plurality of microchannels may contain, for example, 2, 10, 100, 1000 or more channels capable of operating in parallel. In preferred embodiments, the microchannels are arranged in parallel arrays of planar microchannels, for example, at least 3 arrays of planar microchannels. In some preferred embodiments, multiple microchannel inlets are connected to a common header and/or multiple microchannel outlets are connected to a common footer. During operation, heat exchange microchannels (if present) contain flowing heating and/or cooling fluids. Nonlimiting examples of this type of known reactor usable in the present invention include those of the microcomponent sheet architecture variety (for example, a laminate with microchannels) exemplified in U.S. Pat. Nos. 6,200,536 and 6,219,973 (both of which are incorporated by reference). Performance advantages in the use of this type of reactor architecture for the purposes of the present invention include their relatively large heat and mass transfer rates, and the substantial absence of any explosive limits. Pressure drops can be low, allowing high throughput and the catalyst can be fixed in a very accessible form within the channels eliminating the need for separation. In some embodiments, a reaction microchannel (or microchannels) contains a bulk flow path. The term "bulk flow path" refers to an open path (contiguous bulk flow region) within the reaction chamber. A contiguous bulk flow region allows rapid fluid flow through the reaction chamber without large pressure drops. Bulk flow regions within each reaction channel preferably have a cross-sectional area of $5 \times 10^{-8}$ to $1 \times 10^{-1}$ m$^2$, more preferably $5 \times 10^{-7}$ to $1 \times 10^4$ m$^2$. The bulk flow regions preferably comprise at least 5%, more preferably at least 50% and in some embodiments, 30-99% of either 1) the interior volume of a microchannel, or 2) a cross-section of a microchannel.

In many preferred embodiments, the microchannel apparatus contains multiple microchannels, preferably groups of at least 5, more preferably at least 10, parallel channels that are connected in a common manifold that is integral to the device (not a subsequently-attached tube) where the common manifold includes a feature or features that tend to equalize flow through the channels connected to the manifold. Examples of such manifolds are described in U.S. patent application Ser. No. 10/695,400, filed Oct. 27, 2003 which is incorporated herein. In this context, "parallel" does not necessarily mean straight, rather that the channels conform to each other. In some preferred embodiments, a microchannel device includes at least three groups of parallel microchannels wherein the channel within each group is connected to a common manifold (for example, 4 groups of microchannels and 4 manifolds) and preferably where each common manifold includes a feature or features that tend to equalize flow through the channels connected to the manifold.

In devices with multiple manifolds, the invention can be characterized by the volume ratio of one manifold to its connecting microchannels, or characterized by the volumetric sum of plural manifolds and their connecting microchannels. However, if connecting channels are connected to a header and footer, then both the header and footer must be included in the calculation of manifold volume. The volume of the submanifold is included in the volume of the manifold.

Heat exchange fluids may flow through heat transfer microchannels adjacent to process channels (such as reaction microchannels), and can be gases or liquids and may include steam, oil, or any other known heat exchange fluids—the system can be optimized to have a phase change in the heat exchanger. In some preferred embodiments, multiple heat exchange layers are interleaved with multiple reaction microchannels. For example, at least 10 heat exchangers interleaved with at least 10 reaction microchannels and preferably there are 10 layers of heat exchange microchannel arrays interfaced with at least 10 layers of reaction microchannels. In other preferred embodiments, the ratio of heat exchange microchannels or layers to reaction microchannels or layers may vary, with some being in the range of 0.1 to 1 and some being in the range of 1 to 10. Each of these layers may contain simple, straight channels or channels within a layer may have more complex geometries. In preferred embodiments, one or more interior walls of a heat exchange channel, or channels, has surface features.

A general methodology to build commercial scale microchannel devices is to form the microchannels in the shims by different methods such as etching, stamping etc. These techniques are known in the art. For example, shims may be stacked together and joined by different methods such as chemical bonding, brazing etc. After joining, the device may or may not require machining.

In some embodiments, the inventive apparatus (or method) includes a catalyst material. The catalyst may define at least a portion of at least one wall of a bulk flow path. In some preferred embodiments, the surface of the catalyst defines at least one wall of a bulk flow path through which passes a fluid stream. During a heterogeneous catalysis process, a reactant composition can flow through a microchannel, past and in contact with the catalyst.

In some embodiments, the width of each connecting microchannel is substantially constant along its length and each channel in a set of connecting channels have substantially constant widths; "substantially constant" meaning that flow is essentially unaffected by any variations in width. For these examples the width of the microchannel is maintained as substantially constant. Where "substantially constant" is defined within the tolerances of the fabrication steps.

Microchannels (with or without surface features) can be coated with catalyst or other material such as sorbent. Catalysts can be applied onto the interior of a microchannel using techniques that are known in the art such as wash coating. Techniques such as CVD or electroless plating may also be utilized. In some embodiments, impregnation with aqueous salts is preferred. Typically this is followed by heat treatment and activation steps as are known in the art. Other coatings may include sol or slurry based solutions that contain a catalyst precursor and/or support. Coatings could also include reactive methods of application to the wall such as electroless plating or other surface fluid reactions.

In some preferred embodiments methanol is reacted over a formaldehyde synthesis catalyst to form formaldehyde. Preferred formaldehyde synthesis catalysts comprise oxygen compounds (oxides) comprising Mo, Ti, V, and optionally Fe. In some preferred embodiments, the oxide is disposed on a substrate. The substrate may be the wall of a microchannel. In some embodiments, the substrate is a stable, porous support such as an aluminosilicate. The oxides can be supported on a mesoporous material, either as a powder, pellet, etc., or as a wall coating on a microchannel wall (for example, a mesoporous layer disposed between a microchannel wall and the oxide. An aluminosilicate or a mesoporous material (such as SBA-15) may be mixed with a metal oxide (for example titania). In some embodiments, the oxide catalyst comprises at least 2 wt % V or at least 6 wt % V, in some embodiments 5 to 20 wt % V. These weight % do not include the weight of any underlying channel walls or mesoporous matrix, but it does include the weight of other materials such as aluminosilicates, oxide coatings, etc. For pellets, the entire mass of the pellet is included. In some embodiments, the oxide catalyst comprises at least 2 wt % Mo or at least 6 wt % Mo, in some embodiments 5 to 20 wt % Mo. In some embodiments, the oxide catalyst comprises at least 4 wt % Ti or at least 10 wt % Ti, in some embodiments 5 to 60 wt % Ti, in some embodiments 10 to 40 wt % Ti. The invention is intended to include any combination of these values, for example, in some embodiments at least 2 wt % Mo, 2 wt % V, and at least 4 wt % Ti. In some embodiments, the oxide catalyst comprises at least 0.5 wt % Fe or at least 1 wt % Fe, in some embodiments 1 to 10 wt % Fe.

In some preferred embodiments, a formaldehyde synthesis catalyst can be made by impregnating a titania-containing powder with an aqueous molybdate solution. Iron can be added either by impregnation (for example into a Mo/Ti material or V/Ti material or Mo/V/Ti) or ion exchange with Mo/Ti or V/Ti or Mo/V/Ti. V oxide can also be impregnating into Mo/Ti, or V/Ti, or Mo/V/Ti.

In some preferred embodiments, a surface passivating layer (for example, of silica) is first coated on the structured wall in a microreactor prior to the coating of the formaldehyde synthesis catalyst.

The invention includes processes of conducting chemical reactions and other unit operations in the apparatus described herein. The invention also includes prebonded assemblies and laminated devices of the described structure and/or formed by the methods described herein. Laminated devices can be distinguished from nonlaminated devices by optical and electron microscopy or other known techniques. The invention also includes methods of conducting chemical processes (such as chemical reactions) in the devices described herein. In some embodiments, the methods include the steps of flowing a fluid through a manifold and conducting a unit operation in the connecting channels (if the manifold is a header, a fluid passes through the manifold before passing into the connecting channels; if the manifold is a footer then fluid flows in after passing through the connecting channels). In some preferred embodiments, the invention includes non-reactive unit operations, including heat exchange, mixing, chemical separations, or solid formation processes within the microchannels, phase change unit operations such as condensation and evaporation; such processes are generally termed chemical processes, which in its broadest meaning (in this application) includes heat exchange, but in preferred embodiments is not solely heat exchange but includes a unit operation other than heat exchange and/or mixing.

The invention also includes processes of conducting one or more unit operations in any of the apparatus or methods of the invention. Suitable operating conditions for conducting a unit operation can be identified through routine experimentation. Reactions of the present invention include: acetylation, addition reactions, alkylation, dealkylation, hydrodealkylation, reductive alkylation, amination, ammoxidation aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, dehalogenation, dehydrogenation, oxydehydrogenation, dimerization, epoxidation, esterification, exchange, Fischer-Tropsch, halogenation, hydrohalogenation, homologation, hydration, dehydration, hydrogenation, dehydrogenation, hydrocarboxylation, hydroformylation, hydrogenolysis, hydrometallation, hydrosilation, hydrolysis, hydrotreating (including hydrodesulferization HDS/HDN), isomerization, methylation, demethylation, metathesis, nitration, oxidation, partial oxidation, polymerization, reduction, reformation, reverse water gas shift, Sabatier, sulfonation, telomerization, transesterification, trimerization, and water gas shift. For each of the reactions listed above, there are catalysts and conditions known to those skilled in the art; and the present invention includes apparatus and methods utilizing these catalysts. For example, the invention includes methods of amination through an amination catalyst and apparatus containing an amination catalyst. The invention can be thusly described for each of the reactions listed above, either individually (e.g., hydrogenolysis), or in groups (e.g., hydrohalogenation, hydrometallation and hydrosilation with hydrohalogenation, hydrometallation and hydrosilation catalyst, respectively). Suitable process conditions for each reaction, utilizing apparatus of the present invention and catalysts that can be identified through knowledge of the prior art and/or routine experimentation. The invention includes any one or any combination of the above-cited reactions. To cite one example, the invention provides a Fischer-Tropsch reaction using a device (specifically, a reactor) having one or more of the design features described herein. In a preferred embodiment, the invention comprises formaldehyde synthesis over a formaldehyde synthesis catalyst in a microchannel.

Pressure drop through a microchannel or set of connecting microchannels is preferably less than 500 psi (35 bar), more preferably less than 50 psi (3.5 bar) and in some embodiments is in the range of 0.1 to 20 psi (0.007 to 1.4 bar). In some embodiments, wherein the manifold is a header, the pressure drop in the manifold, as measured in psi between the header inlet and the connecting channel inlet (corresponding to a header outlet) having the lowest pressure, is less than (more preferably less than 80% of, more preferably less than half (50%) of, and in some embodiments less than 20% of) the pressure drop through the plural connecting channels (measured as an average pressure drop over the plural connecting channels).

In some preferred embodiments, the manifold volume is less than 80%, or less than 50% (half) in some embodiments 40% or less, and in some embodiments less than 20% of the volume of the plural connecting channels. In some embodiments, the manifold volume is 10% to 80% of the volume of the plural connecting channels. Preferably, the combined volume of all manifolds in a laminated device is 50% or less, in some embodiments 40% or less, of the combined volume of all connecting channels in a device; in some embodiments, 10% to 40%.

Device features can be made by stamping or cutting features through a sheet or sheets; and alternatively or in addition, partial etch or material removal from a sheet can be used to make device features; combinations of cutting and etching can also be used. In some partially etched applications, the depth of the channel is removed from a sheet leaving a wall that intervenes between flow channels, and preferably ribs that support the walls for the differential pressure at temperature and preferably create a high aspect ratio microchannel (width to gap ratio>2). In some embodiments, flow straighteners and modifiers are disposed in an M2M section.

The use of disrupted flow for chemical reactions, separation, or mixing is particularly advantageous in a portion of the connecting channels that is at least 5% of the connecting channel length. The use of disrupted flow (such as flow past an obstacle or over surface features) as applied to mass exchange unit operations (reaction, separation and/or mixing) allow for enhanced performance with process channel gaps in the preferred range of 0.5 mm to 1.5 mm which may enable a more compact device than mass exchange applications with smaller microchannels operating in laminar flow in the connecting channels. As an example for a heterogeneous reaction, the use of disrupted flow to bring reactants to the catalyst on the wall versus laminar diffusion to bring reactants to the catalyst overcomes mass transfer limitations. The effective performance of a catalyst may be 2 or more or 5, or 10, or 100 or 1000 times or more effective than laminar only flow. The more effective mass transfer performance for the catalyst enables a smaller volume for the connecting channels while also permitting channel gaps in the M2M to remain in the preferred region of 0.5 to 1.5 mm and thus minimizes the M2M volume. Chemical separation examples also include absorption, adsorption, distillation, membrane and the like. Chemical separation, mixing, or chemical reactions are particularly optimized for total volume minimization of M2M plus connecting channel volume if at least a portion of the connecting channel is in disrupted flow.

A stage is a section of a channel in which a reactant is added and is defined by a stage length. A stage length (the length from one aperture or inlet to the next aperture or inlet) preferably is in the range of 2.5 mm to 25 cm, more preferably 2.5 mm to 13 cm, and still more preferably 2.5 mm to 2.5 cm. The number of stages can vary from at least 2 to 100 or more (staging can be essentially continuous without a fixed number of stages), in some embodiments from 3 to 75, in some embodiments from 10 to 60 stages. Each stage can have the same length or stages can have different lengths. In some preferred embodiments, contact time is maintained about constant but the length of each stage increases progressively to accommodate the higher flow rate in each stage.

Variance in residence time in each stage is preferably minimized. In some preferred embodiments, at least 90% (more preferably at least 95%, and still more preferably at least 99%, and still more preferably at least 99.5%) of the flow of a stream entering an inlet or aperture has a residence time that varies by 10% or less, more preferably 2% or less, more preferably 1% or less. Residence time distribution of a method can be measured by pulse testing with the use of a tracer or labeled compound. The residence time distribution characteristic of a reactor can be measured using the apparatus test conditions described below. The residence time distribution characteristic of a reactor is characterizable by a measurement in which at least 90% (more preferably at least 95%, and still more preferably at least 99%, and still more preferably at least 99.5%) of the flow of a stream entering an inlet or aperture has a residence time that varies by 10% or less, more preferably 2% or less, more preferably 1% or less. These values may be alternatively stated based on mass average of all fluids (which in some embodiments are gases) that pass through a reactor, where the mass average is based on the mass of the product stream.

For the reaction of methanol with oxygen to make formaldehyde, the reaction is preferably carried out at a temperature from 250° C. to 450° C., more preferably from 345° C. to 420° C. Preferably, oxygen is added through apertures along a microchannel (i.e., staged into a microchannel) to form gas mixtures having an $O_2$ concentration of from 0.1 to 20%, more preferably 0.5 to 6%. These $O_2$ concentrations are typically measured within an entire stage (averaged over the volume of a stage which is the length from one aperture/$O_2$ inlet to the next aperture/inlet) but can also be measured at the outlet of a stage or the outlet of the microchannel (in the case of the last stage). More preferably, the $O_2$ concentration measured at the outlet of a stage or the outlet of the microchannel is 0.01% to 10%, more preferably less than 0.01% to 1%, and still more preferably 0.05% to 0.15%—desirably these oxygen levels are maintained at the exit of each stage, and, in some embodiments throughout the microchannel (meaning in any 1% of volume of the microchannel reaction zone (where catalyst is present and the mixture is at a sufficiently high temperature to react). Methanol feed into the inlet of a reactor can be neat, or can be mixed with inert gases or, in some cases, oxygen. In preferred embodiments, the feed contains 1% to 50% (by mole) methanol, more preferably from 4 to 26%. Contact times (based on feed into the inlet) are preferably 1 second or less for passage through the entire microchannel reactor, and through each stage are preferably 1 to 500 ms, more preferably 1 to 200 ms in each stage.

Methanol conversion in the reactor is preferably at least 50%, more preferably at least 80%, and still more preferably at least 90%, and still more preferably at least 98%. Formaldehyde selectivity is preferably at least 70%, more preferably at least 90%, still more preferably at least 95%, and in some embodiments, in the range of 70 to about 95%.

The method of making formaldehyde can also be characterized by methanol conversion and selectivities, such as formaldehyde selectivity. The apparatus can be characterized by the ability to obtain any of the selectivities and/or conversions (in any combination) described in the descriptions of the invention or Examples, when the apparatus is tested under the following specified test conditions: a contact time of 140 ms, an average reactor temperature of 400 C, inlet pressure of 5 psig (1.34 atm) and for a feed containing 2% $O_2$ and 4% Methanol (balance inerts). For example, apparatus can be characterized by a methanol conversion of at least 75% and a formaldehyde selectivity of at least 95%; or a methanol conversion of at least 75% and a dme selectivity of 1.0% or less, when tested at the above-mentioned test conditions.

In some embodiments, the microchannel reactors have a bulk flow path and two or more wells (preferably with tapered sides in the direction of flow) with each well having a depth to the nadir of the well of 1 μm to 1 cm, more preferably, 10 μm to 5 mm, more preferably 20 μm to 2 mm. Optionally, the wells are partially or completely filled with a structured wall or other mesoporous matrix. In some preferred embodiments, an aperture is present in a wall of a well so that a fluid reactant can be added to the reaction channel. Alternatively, reactant can be added through an aperture in a wall of the reaction microchannel at a location that is not in a well.

Examples

Experimental Study of Methanol Partial Oxidation In Structured Wall Microreactor A structured wall reactor, Microchannel Reactor A, was used for the experimental investigation of methanol partial oxidation to formaldehyde in microchannel reactor. The MICROCHANNEL REACTOR A device is a stainless steel fabricated structured wall reactor that is 3.5" long, 0.57" wide, and 0.05" high. The 0.05" height comprises of a 0.01" flow gap flanked by 0.02" walls (also called plates or shims) on either side (as seen in FIG. 1). Each 0.02" wall is fabricated from two individual 0.01" walls with different structural patterns. The wall closer to the flow gap has surface features (SF) in a "Z" shape with a 45 degree angle at the two vertices. The metal rib as well as the adjacent valley is both 0.015" wide. The farther wall has a "hole" pattern with ~2750 holes (0.012" diameter) on the entire metal surface. These metal plates (shims) were welded together with inlet and outlet headers to form the MICROCHANNEL REACTOR A device. The actual cross section available to the flow at the inlet is 0.34"×0.01" while 3.3" of surface feature section is available for catalyst loading. Cooling channels (0.005" high, 0.34" wide and 3.3" long) were fabricated on the exterior of both the structured wall sets to control the heat release in the device. See FIG. 1. The experiments were carried out over a wide range of conditions to oxygen partial pressures to estimate the impact on CO selectivity. As seen from the data below, lower partial pressure of oxygen helps to lower the CO selectivity.

TABLE 1

Synopsis of impact of oxygen partial pressure on CO selectivity.

| | | | | |
|---|---|---|---|---|
| % MeOH | 6.54% | 6.29% | 6.93% | 4.42% |
| % O2 | 5.94% | 2.34% | 1.17% | 1.37% |
| % N2 | 87.52% | 91.37% | 91.90% | 94.21% |
| Avg T (deg C.) | 362 | 360 | 361 | 360 |
| Inlet Pr (psi) | 4.56 | 7.96 | 6.71 | 5.43 |
| O2 conv | 54.39% | 62.20% | 96.91% | 77.46% |
| MeOH conv | 83.8% | 42.3% | 29.5% | 46.8% |
| Product basis | | | | |
| HCHO sel | 87.9% | 93.5% | 92.0% | 92.5% |
| H2 sel | 0.2% | 0.4% | 0.9% | 1.0% |
| CO sel | 8.4% | 2.4% | 2.2% | 1.9% |
| CO2 sel | 0.9% | 0.3% | 0.7% | 0.9% |

TABLE 1-continued

Synopsis of impact of oxygen partial pressure on CO selectivity.

| DME sel | 1.2% | 1.1% | 1.5% | 1.1% |
|---|---|---|---|---|
| MF sel | 0.8% | 1.4% | 2.1% | 2.2% |
| DMM sel | 0.8% | 1.2% | 1.5% | 1.4% |
| CT (ms) | 197 | 85 | 111 | 109 |

The impact of temperature on the make of by-products DME (dimethyl ether), MF (methyl formate) and DMM (dimethoxy methane) is illustrated next. As seen from the experimental data below, the higher temperature suppresses the formation of MF and DMM.

TABLE 2

Synopsis of impact of temperature on MF selectivity.

| % MeOH | 10.34% | 11.14% | 10.56% |
|---|---|---|---|
| % O2 | 3.29% | 3.27% | 3.28% |
| % N2 | 86.37% | 85.59% | 86.16% |
| Avg T (deg C.) | 361 | 343 | 371 |
| Inlet Pr (psi) | 8 | 4.9 | 5 |
| O2 conv | 72.47% | 50.73% | 83.82% |
| MeOH conv Product basis | 47.70% | 34.90% | 51.90% |
| HCHO sel | 92.40% | 90.40% | 93.30% |
| H2 sel | 0.25% | 0.33% | 0.33% |
| CO sel | 1.80% | 1.80% | 1.80% |
| CO2 sel | 0.07% | 0.08% | 0.10% |
| DME sel | 2.30% | 2.00% | 1.50% |
| MF sel | 1.20% | 1.60% | 1.10% |
| DMM sel | 2.20% | 4.20% | 2.20% |
| CT (ms) | 123 | 130 | 123 |

The impact of reduced contact time was explored experimentally, and a synopsis shown in Table 3. Reducing the contact time from 141 ms to 33 ms improved the formaldehyde selectivity from 91% to 95%.

TABLE 3

Synopsis of short versus long contact time impact on formaldehyde selectivity.

| % MeOH | 4.07% | 3.75% |
|---|---|---|
| % O2 | 2.02% | 1.96% |
| % N2 | 93.92% | 94.28% |
| Avg T (deg C.) | 402 | 403 |
| Inlet Pr (psi) | 4.7 | 21.02 |
| O2 conv | 81.36% | 51.83% |
| MeOH conv Product basis | 74.7% | 44.1% |
| HCHO sel | 91.2% | 95.0% |
| H2 sel | 1.2% | 0.5% |
| CO sel | 5.2% | 2.3% |
| CO2 sel | 1.5% | 0.3% |
| DME sel | 1.2% | 1.2% |
| MF sel | 0.9% | 1.2% |
| DMM sel | 0.0% | 0.1% |
| CT (ms) | 141 | 33 |

Another consideration for the staged addition model is the management of the side products dimethoxymethane (DMM) or methylal, methyl formate (MF), and dimethyl ether (DME). Rapid quench of the product stream essentially reduced the DMM to negligible values. The product quench can be achieved by rapid cooling in a heat exchanger or by using a nitrogen quench. As seen in Table 4 below, this significantly minimizes the formation of DMM.

TABLE 4

Synopsis of impact of product quench on DMM selectivity.

|  |  | N2 dilution, | HE quench |
|---|---|---|---|
| % MeOH | 4.04% | 4.05% | 4.04% |
| % O2 | 2.04% | 2.03% | 2.03% |
| % N2 | 93.93% | 93.92% | 93.93% |
| Avg T (deg C.) | 403 | 402 | 403 |
| Inlet Pr (psi) | 4.73 | 5.7 | 4.69 |
| O2 conv | 83.23% | 78.70% | 79.67% |
| MeOH conv Product basis | 77.8% | 76.0% | 75.0% |
| HCHO sel | 91.6% | 90.6% | 91.3% |
| H2 sel | 1.3% | 1.1% | 1.7% |
| CO sel | 5.1% | 6.3% | 4.9% |
| CO2 sel | 1.3% | 1.0% | 1.9% |
| DME sel | 1.1% | 1.1% | 1.1% |
| MF sel | 0.8% | 1.0% | 0.8% |
| DMM sel | 0.1% | 0.0% | 0.0% |
| CT (ms) | 144 | 143 | 143 |

The production of MF has remained high as compared to the original assessment of the V—Mo Ox/TiO$_2$ catalyst in a powder form (shown in Table 5) at low contact time and very high dilution. This data was obtained in a micro-channel packed bed reactor with cross-sectional area 0.25"×0.06" and catalyst bed length of 1.08".

TABLE 5

Powder catalyst data showing little formation of MF on the V—Mo Ox/TiO$_2$ catalyst at short contact time.

| % MeOH | 2.32% | 0.26% |
|---|---|---|
| % O2 | 1.97% | 0.13% |
| % N2 | 95.38% | 99.57% |
| Temperature (deg C.) | 260 | 260 |
| WHSV (hr−1) | 1.39 | 0.98 |
| MeOH Conversion | 91.15% | 74.63% |
| HCHO Sel | 90.05% | 98.28% |
| CO Sel | 4.80% | 0.00% |
| DME Sel | 3.45% | 1.72% |
| MF Sel | 1.65% | 0.00% |
| DMM Sel | 0.00% | 0.00% |
| Contact time (ms) | 157 | 25 |

Figure 5:
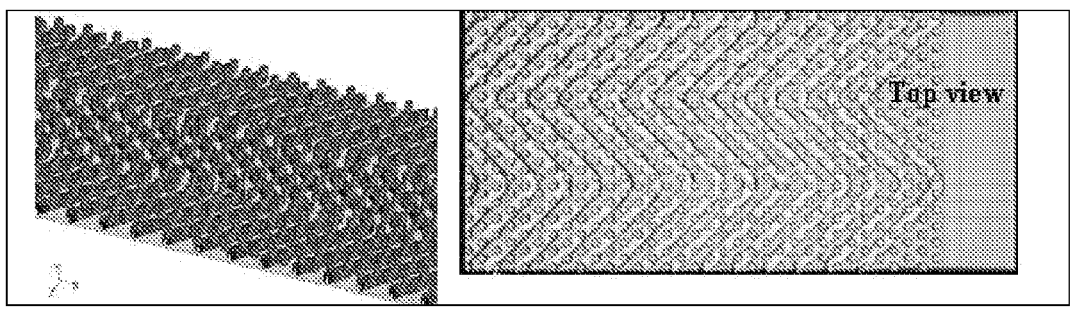
FIG. 5 shows the microchannel reactor with a structured wall that was modeled as described in the Examples section.

In an attempt to understand if there could be other factors to consider, a detailed CFD model of Microchannel Reactor A (described above) was made. The results (based on a uniform application of catalyst) were striking in that some molecules could spend more than 100 times the mean residence time in the recessed areas (wells) of the structure (See FIG. 5). For a reaction such as methyl formate formation, where time is needed for two formaldehyde molecules to react, the large residence time distribution is problematic and can be reduced by minimizing residence time distribution, for example, through a design modification of the structured wall (as described later in the text).

In view of these findings, an improved synthesis process can be based on one or more of the principles of: the staged and controlled addition of a reactant; for formaldehyde the staged composition preferably comprises a source of oxygen, including but not limited to oxygen, air, or enriched air, to reduce yield of undesired products (e.g., CO in the case of formaldehyde synthesis); modestly high temperatures (~>360 C for formaldehyde synthesis) to reduce the formation of the remaining byproducts (e.g. MF, also in the case of formaldehyde synthesis); rapid product quench to reduce or eliminate production of DMM; minimizing RTD; and a structured wall design for reducing dead zones (and also typically retaining catalyst).

Catalyst Preparation:

1. 2% $Fe_2O_3$–12% $V_2O_5$+11% $MoO_3/TiO_2$ (nano-size)

12% $V_2O_5$+11% $MoO_3/TiO_2$ was synthesized by incipient-wetness impregnation. $MoO_3/TiO_2$ was prepared first. 0.528 g ammonium paramolybdate (Alfa, $(NH_4)_6Mo_7O_{24} \cdot 4H_2O$) was dissolved in 5.29 g $H_2O$. The solution was impregnated onto 3.0 g $TiO_2$ nano-powder (200-220 $m^2/g$, Alfa). The powder was dried at 120° C. for 1 h. The impregnation process was repeated once. Subsequently the sample was calcined at 500° C. for 4 hours. For the $V_2O_5$ coating, 0.597 g $NH_4VO_3$ and 1.2 g $H_2C_2O_4$ were dissolved into 6.6 g $H_2O$. The solution was impregnated onto the $MoO_3/TiO_2$ powder. Again, the sample was dried at 120° C. for 1 hour. The impregnation process was repeated until all the vanadium solution was coated on the $MoO_3/TiO_2$ powder. Next the sample was calcined at 450° C. for 4 hours.

Fe was added to the $V_2O_5$+$MoO_3/TiO_2$ catalyst by ion-exchange. 1.5 g 12% $V_2O_5$+11% $MoO_3/TiO_2$ sample was added in 200 ml of 0.1M $FeCl_2$ solution with stirring. The ion-exchange was performed for 20 hours at room temperature. The slurry was then filtered and the solid was washed with $H_2O$ three times. After drying at 120° C., the sample was calcined at 400° C. for 1 hour. The $Fe_2O_3$ content is around 2%.

2. 20% $V_2O_5$+10% $MoO_3/TiO_2$/SBA-15

SBA-15 is a known, silica-based mesoporous material. SBA-15 was prepared as follows. 128.0 g 5N HCl and 272 g $H_2O$ are mixed to yield 400 g of 1.6N HCl solution. 10.7 g of P123 co-polymer was then added and heat to 35-40° C. with stifling. After the P123 was dissolved, 22.7 g tetraethyl orthosilicate (TEOS) was added with stifling. The solution was stirred at 35-40° C. for 24 h. Next the mixture was transferred to a three-neck flask and the temperature increased to 100° C. and held at temperature for 48 hrs. The slurry was filtered and washed with $H_2O$. The solid was dried at 120° C. for 1 h and then calcined at 500° C. for 4 hrs at 2° C./min heating ramp rate. The surface area of the prepared SBA-15 sample was 876 $m^2/g$. Subsequently, 6.25 g titanium iso-propoxide was dissolved in 11.0 g iso-propanol. The solution was impregnated onto 3.0 g SBA-15 powder and dried at 100° C. for 1 hour. The obtained sample was then calcined at 550° C. for 2 hours in air to produce $TiO_2$/SBA-15. Next, 0.70 g ammonium paramolybdate was dissolved in 7.0 g $H_2O$. The solution was dropped onto 4.0 g $TiO_2$/SBA-15. The powder was dried at 120° C. for 1 h and then calcined at 500° C. for 4 hours. For the $V_2O_5$ coating, 1.47 g $NH_4VO_3$ and 2.88 g $H_2C_2O_4$ were dissolved into 15.4 g $H_2O$. The solution was impregnated onto the $MoO_3/TiO_2$/SBA-15 powder. Again, the sample was dried at 120° C. for 1 hour. The impregnation process was repeated twice until all vanadium solution was consumed. Next the sample was calcined at 450° C. for 4 hours. The final catalyst composition was 20 wt % $V_2O_5$, 10 wt % $MoO_3$, 26 wt % $TiO_2$ and 44 wt % SBA-15.

$MoO_3$ Sublimation:

$MoO_3$ sublimation was studied at 450 and 700° C. in flowing 2.5% $H_2O$/air in a tubular reactor. As presented in Table 2, the commercial Fe—Mo—Ox catalyst suffers a weight loss of 25% after 100-hour testing at 700° C. By comparison, significantly lower weight losses are observed for both 2% $Fe_2O_3$-12% $V_2O_5$+11% $MoO_3/TiO_2$ (nano-size) and 20% $V_2O_5$+10% $MoO_3/TiO_2$/SBA-15 catalysts. They are only 8 and 5%, respectively. These results prove that the supported $V_2O_5$+$MoO_3$ catalysts are more resistant to $MoO_3$ sublimation and, hence, more stable than commercial Fe—Mo—Ox catalyst. At 450° C., after 100-hour testing, the weight losses for all three catalysts was less than 2%, which is within experimental error.

$MoO_3$ sublimation was investigated via two methods. The first method involved thermal gravimetric analysis (TGA), whereby, in flowing air weight loss was measured with increasing sample temperature. The second method involved treating the catalysts at 700° C. to an atmosphere of $H_2O$ and air for 100 hrs. A commercial Engelhard $Fe_2O_3$—$MoO_3$ catalyst was used as a reference.

FIG. 1 shows the TGA profiles of the three samples. All the samples lost some weight below 200-300° C., which is attributed to adsorbed $H_2O$. $MoO_3$ will not be vaporized below 310° C. From the profiles, 2% $Fe_2O_3$–12% $V_2O_5$+11% $MoO_3/TiO_2$ and the Fe—Mo catalysts desorbed around 2 wt % water while 20% $V_2O_5$+10% $MoO_3/TiO_2$/SBA-15 desorbed 8.5 wt % in air. With increasing temperature, the Fe—Mo catalyst began to lose additional weight at approximately 425° C. with an additional, more significant weight change above 700° C. The weight losses observed above 425° C. is believed to be due to $MoO_3$ sublimation. By comparison, 2% $Fe_2O_3$–12% $V_2O_5$+11% $MoO_3/TiO_2$ and 20% $V_2O_5$+10% $MoO_3/TiO_2$/SBA-15 began to experience weight loss above 600 and 675° C., respectively. The higher $MoO_3$ sublimation temperatures for the two supported $V_2O_5$+$MoO_3$ catalysts suggest that they are more thermally stable than the commercial Fe—Mo catalyst.

Since $H_2O$ may be present in the feed (and is certainly formed during the reaction) and can promote $MoO_3$ sublimation, we also studied $MoO_3$ sublimation in the presence of $H_2O$. $MoO_3$ sublimation was studied at 700° C. in flowing 2.5% $H_2O$/air in a tubular reactor. As presented in Table 6, the commercial Fe—Mo—Ox catalyst suffers a weight loss of 25% after 100-hour testing at 700° C. By comparison, significantly lower weight losses were observed for both 2% $Fe_2O_3$–12% $V_2O_5$+11% $MoO_3/TiO_2$ and 20% $V_2O_5$+10% $MoO_3/TiO_2$/SBA-15 catalysts, i.e., only 8 and 5%, respectively. These results further suggest that the supported $V_2O_5$+$MoO_3$ catalysts are more resistant to $MoO_3$ sublimation and, hence, more stable than commercial Fe—Mo—Ox catalyst. At 450° C., after 100-hour testing, the weight losses for all three catalysts was less than 2%; well within experimental error.

TABLE 6

$MoO_3$ vaporization of formaldehyde catalysts at 700° C.

| Catalyst | Weight change (%) |
|---|---|
| Fe—Mo-Ox | −25 |
| 2%$Fe_2O_3$—12%$V_2O_5$ + 11%$MoO_3$/$TiO_2$ (nano-size) | −8 |
| 20%$V_2O_5$ + 10%$MoO_3$/$TiO_2$/SBA-15 | −5 |

Catalytic Performance:

Initial performance testing for the catalyst formulations (powder form) was conducted in a packed-bed microchannel reactor with heat exchanger. The inlet cross-sectional area for the microchannel is 0.25"×0.06". Approximately 0.2 g of catalyst (~1" bed length) was used for the testing. Typical testing conditions and performance metrics for the various catalyst formulations involving $MoO_3$, $V_2O_5$ and $TiO_2$ support are summarized in Table 7 below.

TABLE 7

Catalytic performance for selective oxidation of methanol to formaldehyde

| Catalyst | Weight of Catalyst (g) | Reactor Temp. (° C.) | Contact Time (ms) | WHSV (gMeOH/gCat/Hr) | Feed MeOH (%) | Feed H2O (%) | Feed O2 (%) | MeOH Conv. (mol %) | HCHO sel. (%) |
|---|---|---|---|---|---|---|---|---|---|
| 12% V2O5, 11% MoOX/ nano-TiO2 | 0.20 | 260 | 157 | 1.39 | 3.70% | 0.38% | 3.13% | 99.46% | 38.72% |
|  | 0.20 | 260 | 25 | 0.98 | 0.42% | 0.04% | 0.21% | 98.88% | 87.63% |
|  | 0.20 | 250 | 25 | 0.98 | 0.42% | 0.04% | 0.21% | 91.77% | 88.81% |
| 2% Fe, 12% V2O5, 11% MoO3/Nano-TiO2 | 0.17 | 250 | 50 | 7.54 | 5.21% | 0.53% | 4.40% | 70.47% | 94.75% |
|  | 0.17 | 260 | 50 | 7.54 | 5.21% | 0.53% | 4.40% | 96.39% | 87.44% |
|  | 0.17 | 260 | 83 | 4.52 | 5.21% | 0.53% | 4.40% | 99.24% | 81.69% |
|  | 0.17 | 260 | 100 | 3.77 | 5.21% | 0.53% | 4.40% | 100.00% | 76.59% |
|  | 0.17 | 255 | 50 | 7.54 | 5.21% | 0.53% | 4.40% | 82.06% | 93.63% |
| 20% V2O5, 10% MoOX/ TiO2—SBA-15 | 0.15 | 260 | 157 | 1.39 | 2.32% | 0.24% | 1.97% | 91.15% | 90.05% |
|  | 0.15 | 260 | 25 | 0.98 | 0.26% | 0.03% | 0.13% | 74.63% | 98.28% |
|  | 0.15 | 250 | 25 | 0.98 | 0.26% | 0.03% | 0.13% | 52.82% | 97.67% |
| 20% V2O5, 10% MoO3/ TiO2 | 0.20 | 260 | 105 | 2.68 | 5.71% | 0.58% | 4.21% | 94.57% | 87.57% |
|  | 0.20 | 260 | 25 | 1.95 | 0.99% | 0.10% | 0.33% | 78.64% | 91.64% |
|  | 0.20 | 270 | 25 | 1.95 | 0.99% | 0.10% | 0.33% | 72.15% | 91.09% |
|  | 0.20 | 250 | 25 | 1.95 | 0.99% | 0.10% | 0.33% | 59.38% | 96.24% |

Operational Constraint on Oxygen Concentration

Figure 3:
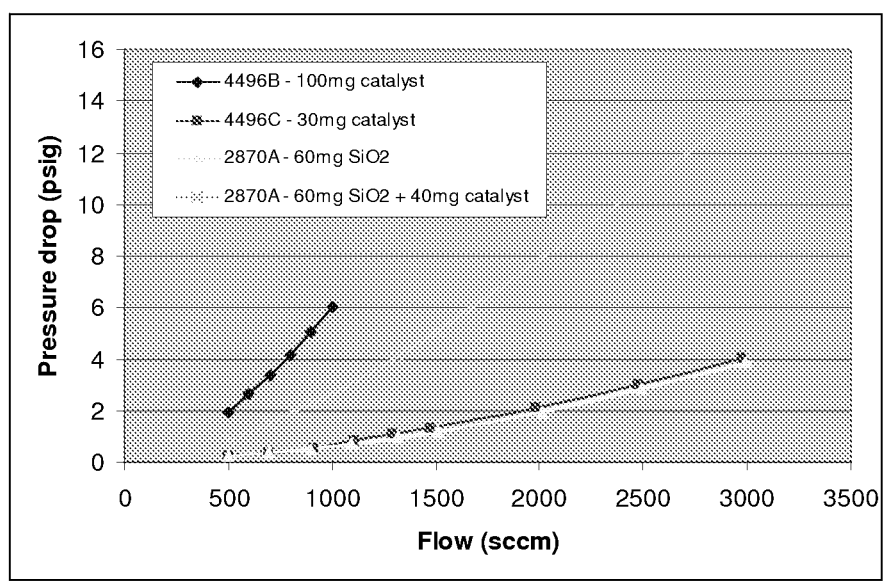
FIG. 3 shows pressure drop in various microchannel reactors used in the examples.

Three different devices designated as 4496B, 4496C and 2870A (same design as the MICROCHANNEL REACTOR A, described in FIG. 1 above, i.e. stainless steel fabricated structured wall reactor, 3.5" long×0.57" wide×0.05" high–a 0.01" flow gap flanked by 0.02" structured walls on either side.) were tested. A V—Mo Oxide/TiO$_2$ catalyst was coated in situ on the structured walls in the reactor. In some cases, an inert SiO$_2$ coating was applied (in situ) on the structured walls prior to the catalyst washcoats using a fill and drain technique. An inert coating, such as silica, is used to minimize the formation of side products (for example, MF, DME and DMM). In the fill and drain approach for in situ washcoating, the device is first heat-treated at 650° C. for 10 hrs. It is then installed vertically for the washcoating process. The device was filled from the bottom with 10% SiO2 using a syringe pump at a flow rate of 10 mL/min. After holding the sol in the device for ~0.5 min, the sol was pumped out. The excess sol in the channel was purged using compressed air. The cooling channel was then washed with water. Subsequently, the device was dried at 120° C. for 1 hour. The coating process was repeated three times. Finally, the device was calcined at 600° C. for 4 hours. Catalyst loading in MICROCHANNEL REACTOR 4496B and 4496 C was approximately 100 mg and 30 mg respectively. MICROCHANNEL REACTOR 2780A had an approximately 60 mg SiO$_2$ layer over which about 40 mg catalyst was loaded. The pressure drop profile (nitrogen cold flow data collected at ambient conditions—room temperature and reactor outlet at atmospheric pressure) in the device is shown in FIG. 3 and indicates that the catalyst coating may have reduced the open area in the main flow gap accessible to the flow.

To perform the partial oxidation experiments, an HPLC pump was used to pump liquid methanol feedstock to a microchannel vaporizer. Some of the early tests used a syringe pump and a tube-in-tube heat exchanger in place of the instrumentation described above. The tube-in-tube vaporizer (heated air/nitrogen flow around methanol is responsible for the vaporization) was replaced to accommodate higher flow rates of methanol (ensure complete vaporization) and to minimize byproduct formation (through better temperature control) in the vaporizer. The vaporized gas along with the feed air (oxygen) and diluent (nitrogen) is then preheated and subsequently mixed in together in 60 μm stainless steel filter (which acts like a static mixer) before feeding to the reactor inlet. Cooling nitrogen is flown in the cooling channels around the device at ~10-15 SLPM. The complete reactor assembly was insulated. Heat tapes were also used to overcome losses to the surroundings. The product stream exiting the reactor is kept at an elevated temperature of ~120° C. to prevent the formation of para-formaldehyde. The off-gas was taken to an absorber where majority of the components are absorbed in water. The off-gas from the absorber was then sent to an Agilent micro GC for analysis. The liquid collected in the absorber during the run was then analyzed using traditional Agilent 6890 GC and titration. Samples are analyzed for methanol, formaldehyde (titration), dimethyl ether (DME), methyl formate (MF), and methylal (DMM). Experiments were carried out over a range of conditions summarized below:

Temperatures from 250° C. to 450° C., particularly 345 to 420° C.

Feed O$_2$ concentrations from 0.1% to 20%, particularly 0.5 to 6%

Feed MeOH concentrations from 1% to 50%, particularly 4 to 26%

Contact times ranging from 10-500 ms, particularly 30-200 ms.

The microchannel reactor tests were carried out to simulate a single stage of oxygen addition. Therefore, the methanol feed was mixed with oxygen (from air) at the reactor inlet prior to the reaction over the V—Mo Ox/TiO$_2$ catalyst. Typical experimental data from the device 2870A is shown in Table 8 below. Approximately 90% of the data collected in these experiments had an acceptable carbon balance (ratio of moles of Carbon leaving the reactor to that entering the reactor) within ±2%.

TABLE 8

Microchannel Testing Results

| % MeOH | 4.93% | 10.84% | 15.98% | 12.83% | 13.90% | 6.06% | 25.58% | 4.29% | 3.94% |
|---|---|---|---|---|---|---|---|---|---|
| % O2 | 0.57% | 2.35% | 1.82% | 1.47% | 3.02% | 2.50% | 15.71% | 2.21% | 2.21% |
| % N2 | 94.50% | 86.80% | 82.20% | 85.70% | 83.08% | 91.44% | 58.72% | 93.50% | 93.85% |
| Avg T (deg C.) | 381 | 360 | 347 | 361 | 382 | 402 | 381 | 402 | 419 |

TABLE 8-continued

Microchannel Testing Results

| Inlet Pr (psi) | 23.58 | 10.49 | 5.3 | 5.47 | 6.24 | 8.7 | 3.64 | 5.65 | 5.06 |
|---|---|---|---|---|---|---|---|---|---|
| O2 conv | 95.57% | 80.65% | 89.18% | 96.40% | 93.87% | 89.03% | 65.18% | 90.66% | 93.86% |
| MeOH conv | 21.7% | 35.2% | 17.8% | 20.1% | 38.8% | 64.5% | 72.5% | 85.5% | 87.3% |
| Product basis | | | | | | | | | |
| HCHO sel | 92.6% | 92.8% | 90.3% | 91.3% | 93.0% | 93.3% | 88.3% | 89.8% | 87.8% |
| H2 sel | 1.2% | 0.4% | 0.4% | 0.6% | 0.9% | 1.6% | 0.4% | 3.0% | 4.7% |
| CO sel | 2.7% | 1.5% | 1.4% | 1.6% | 1.8% | 3.5% | 5.9% | 7.0% | 8.4% |
| CO2 sel | 0.5% | 0.3% | 0.3% | 0.4% | 0.6% | 1.1% | 0.7% | 2.1% | 3.0% |
| DME sel | 1.8% | 1.6% | 2.0% | 2.0% | 1.5% | 0.8% | 1.2% | 0.6% | 0.5% |
| MF sel | 1.4% | 1.6% | 2.6% | 2.5% | 1.8% | 0.8% | 1.5% | 0.4% | 0.3% |
| DMM sel | 1.0% | 2.2% | 3.3% | 2.1% | 1.4% | 0.5% | 2.4% | 0.1% | 0.1% |
| CT (ms) | 34 | 75 | 112 | 113 | 116 | 85 | 242 | 144 | 141 |

Figure 4:
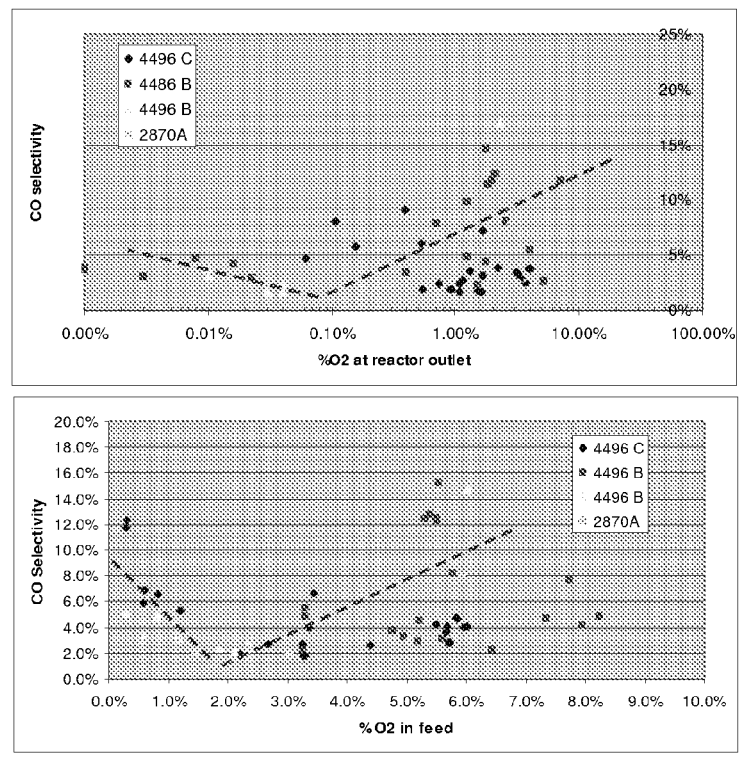
FIG. 4 shows the dependence of CO selectivity on $O_2$ partial pressure in the formaldehyde synthesis reactions from the Examples section.

The testing data was first analyzed for CO selectivity (since CO formed via oxidation of formaldehyde is the major loss product). It was found that the CO selectivity decreased linearly with lowering of oxygen partial pressure (as is expected from the proposed reaction mechanism). However, at very low oxygen partial pressures in the feed (<1%), a higher CO selectivity is observed (see FIG. 4a) indicating a change in the reaction pathway. Hence to minimize the CO selectivity, a window of operation in terms of the feed oxygen partial pressure is proposed where the feed oxygen concentration is desirable in the 1-10% range, more so in the 1-5% range and even more in the 1-2% range. Since the experiments mimic a single stage in the overall reactor, these local partial pressure ratio ranges represent those oxygen partial pressures desirable near the beginning of each stage to provide the lowest CO selectivity under the chosen formaldehyde synthesis conditions.)

The same data was also analyzed in terms of the oxygen partial pressure at the reactor outlet (i.e. end of $1^{st}$ stage). In this case too, the CO selectivity was found to decrease with lower oxygen partial pressure at the reactor outlet but again was found to increase when oxygen partial pressure at the reactor outlet was less than 0.1% (see FIG. 4b). Hence, to eliminate the oxygen starved conditions which contribute significantly to CO formation, an exit $O_2$ concentration in the range 0.01%-10%, more so in the 0.01-1% range and even more in the 0.05-0.15% range is desired at all stages in the reactor. i.e. these constraints imposed on local values of oxygen partial pressure at the inlet and outlet of this experimental reactor (i.e. $1^{st}$ stage in the multi-stage reactor) should also hold for the remainder of the oxygen-feed stages in the reactor. Hence, it is important to control the amount of oxygen fed to the reactor at each of the inter-stage addition points.

Characterization of Reactor Performance: Enhanced Structured Wall Design

Residence Time Distribution in Structured Wall Devices

In a structured wall reactor, the convective flow brings the reactant molecules in contact with the structured wall and the molecules then diffuse into the surface features (aided by some convective component). Reaction occurs at the wall surface (catalyst layer) and the products diffuse (aided by some convective component) into the main flow gap and then are carried out of the reactor by the convective flow. Residence time distribution (RTD) provides a useful estimate of the time spent by the molecules in the reactor.

The MICROCHANNEL REACTOR device contained the following layers in sequence: wall, hole layer, z-shaped surface feature layer, bulk flow path, z-shaped surface feature, hole layer, wall. In order to characterize the RTD of fluids flowing in the MICROCHANNEL REACTOR device, 3D computational fluid dynamics (CFD) simulations of the MICROCHANNEL REACTOR A geometry were carried out using commercial software. Use of the symmetry boundary condition allows only half of the flow gap (shown in FIG. 1) to be simulated. The "holes" and "Z-shaped surface features" in the structured wall were modeled in all detail to capture the "true" flow pattern in the device (see FIG. 5). Continuity and momentum conservation equations for the fluid were solved using a finite volume method.

CFD simulations revealed that the majority of the flow passes through the main channel. A significant fraction of the flow is also seen entering the recessed portions of the "Z-shaped" surface feature shim. However, very little (convective) flow is generated in the "holes" shim. Modeling showed that several holes in the hole-containing shim have a residence time over 500 s, which is several orders of magnitude higher than the average residence time (of ~10 ms) based on the volume of the flow channel. The residence time distribution in the "Z-shaped" surface feature layer is very close to that seen in the actual flow gap.

Figure 6:
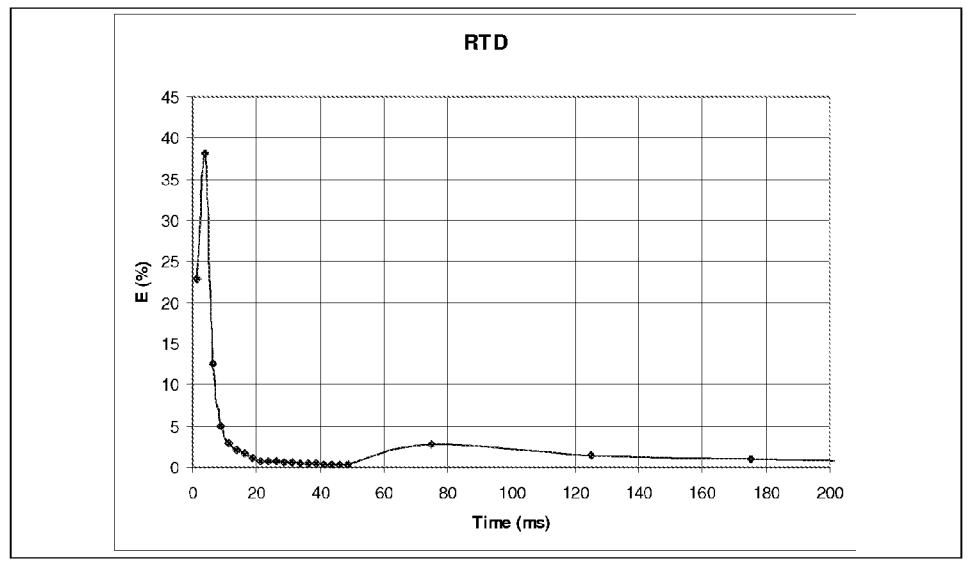
FIG. 6 shows residence time distribution (RTD) for a structured wall a microchannel reactor as described in the Examples.

A summary plot of the RTD behavior in the MICROCHANNEL REACTOR A device is shown in FIG. 6. The first peak around the 10 millisecond (ms) value corresponds to the average contact time based on the flow gap volume. The following tail depicts the recirculation provided by the "Z-shaped" surface features. The $2^{nd}$ peak (around the 80 ms value) and the following tail is representative of the large residence time in the "holes" shim. The long tail with residence times of the order of several minutes is not shown here. In an ideal flow reactor, all reactant molecules experience the same residence time (the corresponding residence time distribution would be a Dirac delta function). Hence, a residence time distribution with a non-zero variance (such as the one shown in FIG. 6) indicates dispersion of the fluid molecules and of flow maldistribution.

Figures 7A, 7B:
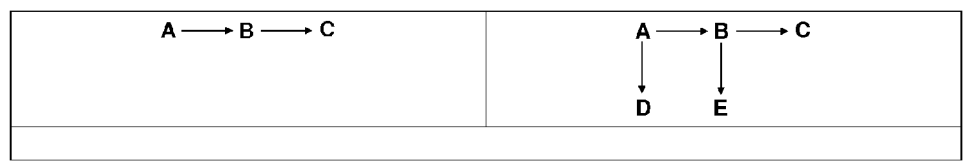
FIG. 7 shows (a) series and (b) series-parallel reactions.

The large disparity of residence times is detrimental for series (see FIG. 7a) and/or series-parallel reactions (see FIG. 7b) where the product of interest is the intermediate in the reaction sequence (in this case 'B'). Examples for the series and/or series-parallel reactions include (but are not limited to) oxidation, partial oxidation, hydrogenation, and nitration reactions. In particular, for the case of methanol partial oxidation A=methanol, B=formaldehyde, C=carbon monoxide, D=dimethyl ether, E=methyl formate (additional loss product DMM formed by reaction of A & B is not depicted in FIG. 7b).

Figure 8:
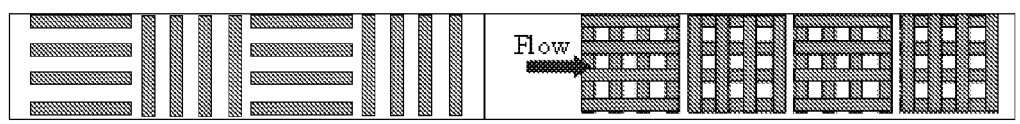
FIG. 8 is a top view of a structured wall (a—single layer; b—pattern with 2 layers).

The pockets (locations within the reactor) with large residence time are primary generators of the undesirable product(s) (for example, C & E) which translates to a loss of selectivity for towards the desired product (B). Such a situation is highly undesirable for achieving high productivity and high selectivity of formaldehyde. In order to illustrate this for methanol partial oxidation, a structured wall reactor with a simple pattern shown in FIG. 8 was modeled.

Several shim layers (typically ranging from 2-50) of alternate patterns are used to create a structured wall. Reactive CFD simulations of such a structured wall (with 30 layers) were carried out for formaldehyde synthesis (a series-parallel reaction network; FIG. 7). Here, methanol is the reactant, formaldehyde the desired product, carbon monoxide, dimethyl ether and methyl formate the undesired series products, and dimethoxy methane is the other undesired product. A 0.1" long flow-by section was included in the model to make the flow fully developed at the leading edge of the SW. A 0.05" long flow-by section was included after the SW reaction zone.

Figure 9:
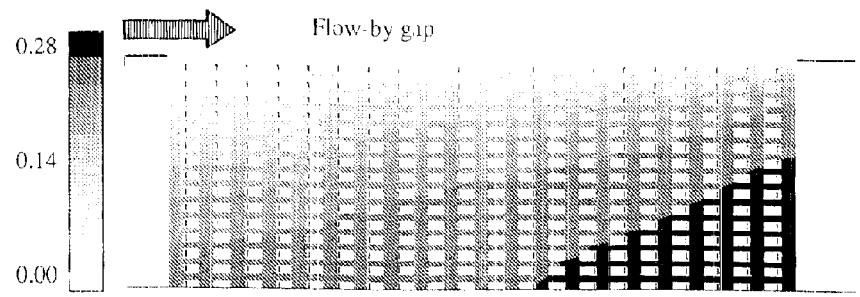
FIG. 9 shows the mass fraction contours of formaldehyde in a structured wall reactor without tapered walls. The regions of high formaldehyde concentration (the darker regions to the lower right) are also the areas of high residence time, highly prone to the formation of undesired side products.

Simulations indicate accumulation of formaldehyde (HCHO) at the dead ends at the bottom of the structured wall as shown in FIG. 9. These zones are also associated with very low convective flow velocities and therefore high residence times. Hence, these areas tend to favor the secondary reactions leading to undesirable side-products such as CO, DME, MF and DMM. The mass fractions contours for these undesired products closely follow the HCHO contours of FIG. 9.

CFD investigations of flow in such a structured wall have revealed convective velocities of 0.1-20% of those in the flow-by gap. However, the dead zones mentioned above also have significant recirculation and a very low effective convective velocity. These lead to zones with large undesired reactions that make it difficult to meet high productivity targets at high selectivities (for example, >95% yield of formaldehyde).

Figure 10:
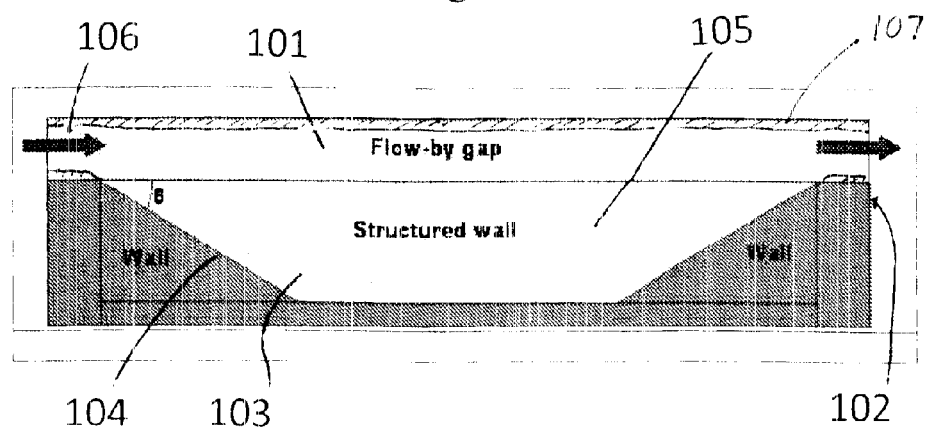
FIG. 10 is a schematic view of a tapered structured wall reactor.

To facilitate the convective flow of the products/reactants from the dead zones within the structured wall, a tapering structured wall pattern is proposed as illustrated in FIG. 10. The taper at both the ends is important and serves to minimize the formation of recirculation wakes and maintain a convective flow velocity component along the structured wall depth. The angle of the taper ($\theta$, measured from the bottom of the flow-by gap to the bottom of the structured wall) can vary from 1 deg to 90 deg. Larger taper angles allow more volume of structured wall and hence higher catalyst loading but are less effective in stabilizing the convective flow component along the bottom of the structured wall. A desired angle of taper could be from 10° to 80°, more preferably from 20° to 70° and even more so from 30° to 60°.

Figure 11:
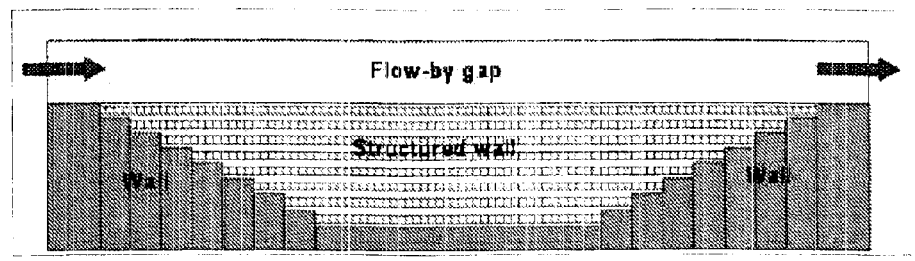
FIG. 11 shows a tapered structured wall reactor using stairsteps.

The taper is most effective in the direction of the flow, but may also be used in the perpendicular direction. In practice, the taper can be achieved, for example, by a series of stair-step structured wall patterns. See FIG. 11. The number of steps required to achieve this would depend on the catalyst loading and the structured wall depth. The number of steps would be at least 2, preferably at least 3 in some embodiments at least 5, and in some embodiments 3 to 30 steps.

Figure 12:
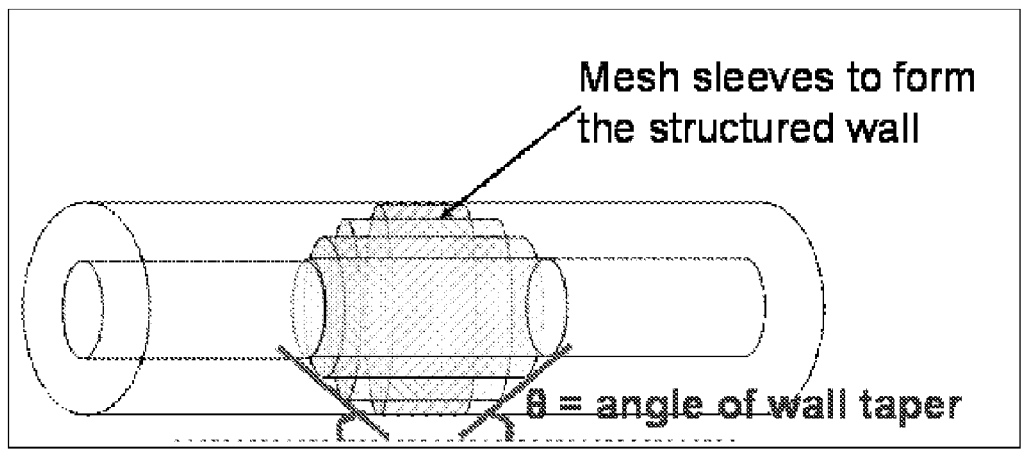
FIG. 12 shows a tapered structured wall reactor using stairsteps in a cylindrical geometry.

An analogous structured wall mesh with the taper can be created in cylindrical channel geometry by using mesh sleeves. Similar to the adhesion of the stack of plates in a rectangular channel; one can envision the stacking and adhesion of cylindrical mesh sleeves to form the structured wall in a cylindrical channel geometry. See FIG. 12. Similar structures could also be made in triangular prisms and other geometrical shapes.

Special Case of Angled Structured Wall Patterns:

In the structured wall discussed above, the flow is perpendicular to the face of the structured wall. In this case the angle of incidence ($\delta$, measured between the direction of flow to a face of the structured wall in the top-most layer of the structured wall, where "top-most" means adjacent to the bulk flow path) is 0°. Structured walls can also be fabricated with varying angles of incidence ranging from 0 deg to 90 deg, preferably from 10 deg to 45 deg and even more preferably from 20 to 30 deg. These angled structured walls are an advantage over those parallel or perpendicular to the flow because they help to introduce an additional convective flow component in the deep structured wall by directing the flow momentum into the structure.

Figure 13:
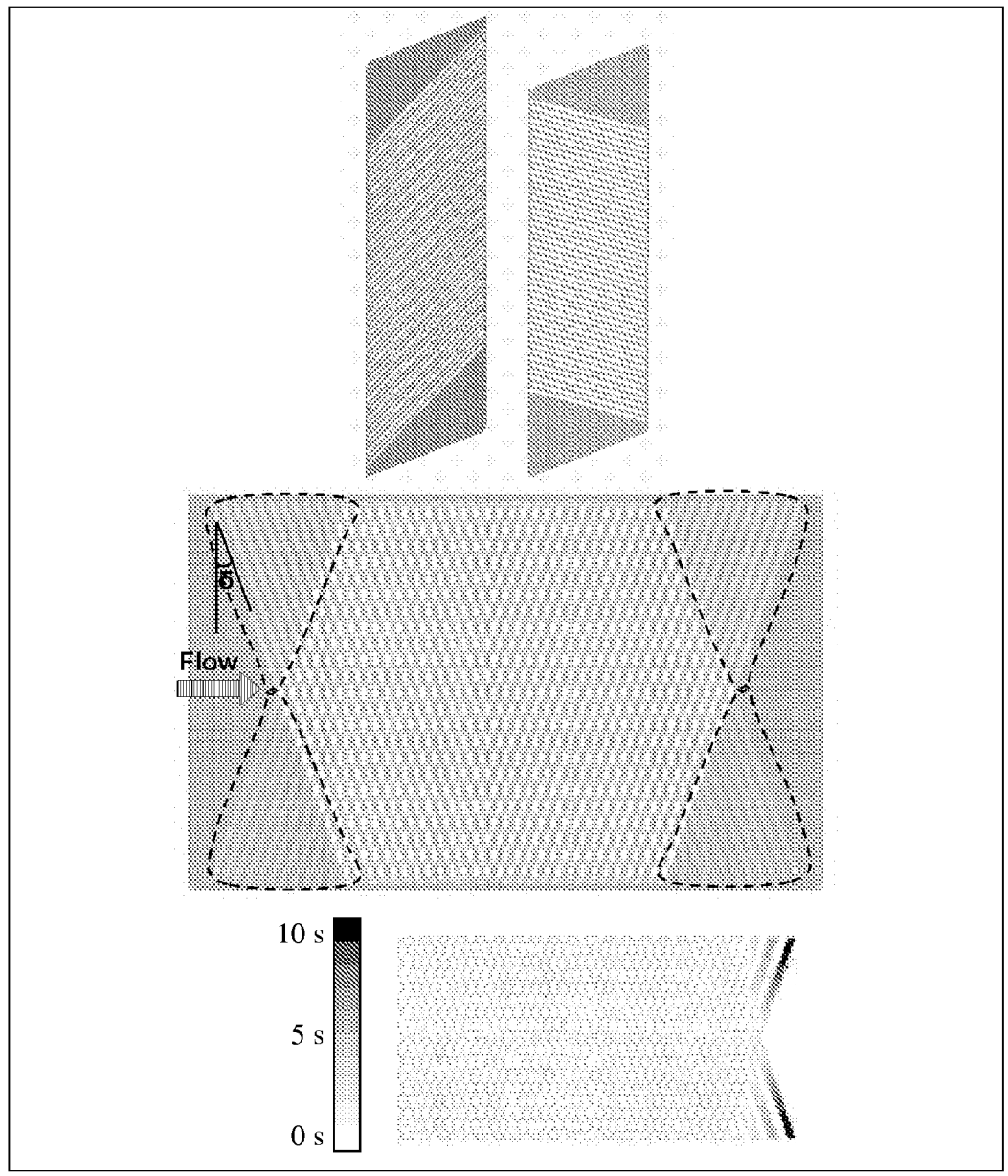
FIG. 13 shows an angled structured wall (open areas are indicated in white). Panel a shows individual shims and an alternate stacking pattern. Panel b shows a top view (dotted line mark the dead-zones). Panel c shows residence time distribution in dead-zones near exit (half shim).
Figure 14:
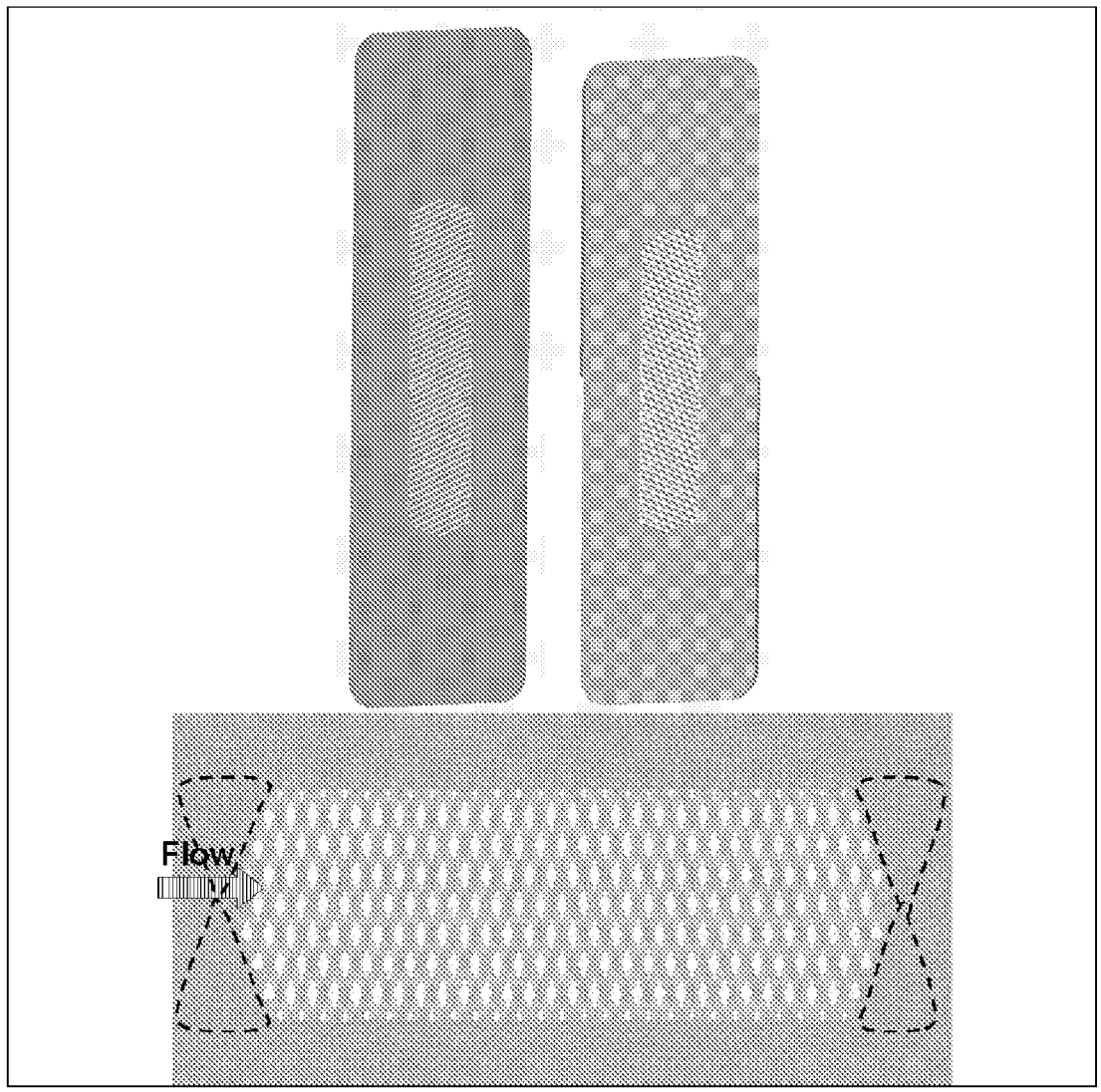
FIG. 14 shows an angled structured wall with taper. Top Panel: individual shims and the alternate stacking pattern. Bottom Panel: assembly top view (dead-zones are eliminated).

In a reactor in which the wall adjacent to a bulk flow path is angled in the direction of flow, it can be seen that the angle can cause the appearance of additional dead-zones (overlapping regions, indicated by the dashed lines in FIG. 13). This is because these regions have limited or no connectivity with the flow areas below the wall. These dead zones have a high residence time and hence a higher rate of formation for undesired products (as discussed above). In order to alleviate the dead-zone formation, the pattern on the structured wall shim can be modified by introducing an inlet and outlet "taper" pattern (tapered in the direction of flow) on the structured wall shim as shown in FIG. 14 (top). The resulting assembled stack, FIG. 14 (bottom), is devoid of any dead-zones and hence is expected to enhance the performance of angled structured walls for series and/or series-parallel reactions where an intermediate is the desired product.

The tapering along the depth of the structured wall (as described above) can also be used in conjunction with this tapered angled structured length wall pattern.

It is recognized that the described structured wall designs which reduce the distribution in residence times within a microchannel may be used for any chemical reaction and have particular advantage for series reactions such as partial oxidation reactions where long reaction times for some molecules reduces the overall selectivity to desired products.

The described structured wall design which improves the residence time distribution have specific advantage for reactions such as Fischer Tropsch reactions and the production of: ethylene oxide, acrylic acid, acrylonitrile, and styrene. In the case of a Fischer Tropsch reaction, the product distribution may be tailored to reduce the formation of very high molecular weight hydrocarbons by improving the residence time distribution.

Reactor Design with Staged Oxygen Addition for Superior Formaldehyde Yield

The data generated from the MICROCHANNEL REACTOR A (i.e. stainless steel fabricated structured wall reactor, 3.5" long×0.57" wide×0.05" high–a 0.01" flow gap flanked by 0.02" structured walls on either side) was used to model the methanol partial oxidation reaction network. This 5 reaction network (see below) is similar to that proposed by Diakov et al (Chem. Eng. Sci., v57, p1563-1569, 2002) and Deshmukh et al (App. Cat. A, v289, p240-255, 2005).

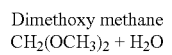
Dimethoxy methane
$CH_2(OCH_3)_2 + H_2O$

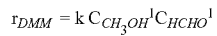
$r_{DMM} = k\, C_{CH_3OH}^1 C_{HCHO}^1$

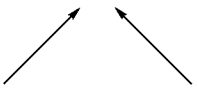

-continued

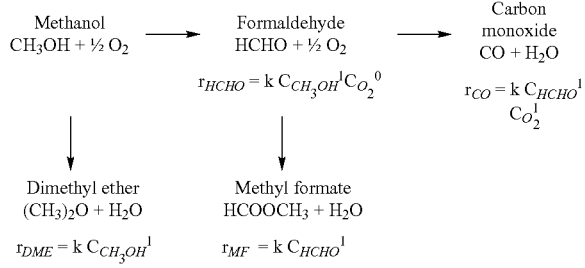

$$\text{Methanol } CH_3OH + \tfrac{1}{2}O_2 \rightarrow \text{Formaldehyde } HCHO + \tfrac{1}{2}O_2 \rightarrow \text{Carbon monoxide } CO + H_2O$$

$$r_{HCHO} = k\, C_{CH_3OH}^{1} C_{O_2}^{0} \qquad r_{CO} = k\, C_{HCHO}^{1} C_{O_2}^{1}$$

$$\downarrow \qquad\qquad \downarrow$$

$$\text{Dimethyl ether } (CH_3)_2O + H_2O \qquad \text{Methyl formate } HCOOCH_3 + H_2O$$

$$r_{DME} = k\, C_{CH_3OH}^{1} \qquad r_{MF} = k\, C_{HCHO}^{1}$$

Based on the methanol partial oxidation reaction stoichiometry and kinetics, the reaction product HCHO has a $0^{th}$ order dependence on oxygen whereas the main loss product CO has a $1^{st}$ order dependence in oxygen (as is also evident from the experimental testing data in the microchannel reactor presented above). Hence a step-by-step or staged addition of oxygen to the reaction mixture will limit the oxygen available for reaction with HCHO (after the methanol oxidation to formaldehyde) thereby minimizing the selectivity to CO. Other loss products viz. MF and DMM can be controlled by carrying out reactions at moderately high temperatures (to minimize their rates but not offsetting the relative rates of CO and HCHO formation).

This reaction model was implemented in a one dimensional computer model developed to simulate addition of oxygen (in air) reactant stage-wise along the length of the reactor microchannel. The stage-wise addition of air lowers the local oxygen partial pressure to depress the formation of carbon monoxide (as described above). The yield was increased by operating at low pressure.

Using the kinetic model from the experimental data on a V—Mo Oxide/$TiO_2$ catalyst, a 1D multi-stage reactor with staged oxygen addition was modeled. Important parameters such are feed flow rates for each stage, stage-length, temperature and catalyst loading. Several such stages 2 to 100 are modeled to maximize the yield of formaldehyde (yield=conversion×selectivity and hence would imply maximizing both.)

A typical stage length ranges from 0.1" to 10", preferably from 0.1" to 5" and more preferably from 0.1" to 1". The number of stages for addition of oxygen (air) to the reacting stream can vary from at least 2 (for low yield targets) up to 100 (for high yield targets), preferably from 5 to 75, and in some cases from 10 to 60 stages. In practice this staged addition may be achieved by active (metered) or passive (resistance controlled jets) addition of air (or other oxygen source). Tunable parameters to control the product yield include (but are not limited to) length, temperature, catalyst loading, feed fraction of air for each stage. Catalyst loading per unit length and length of the stage can be varied with for each stage to maintain a pre-defined yield. Temperature can be controlled to decrease the selectivity to MF and DMM while feed fraction of air is controlled to limit the CO selectivity. All the factors can be varied in tandem to achieve a pre-defined (target) yield. The choice of these factors is not obvious and could vary with reaction, however, a general guideline can be provided as illustrated here. It should be understood that the reactor and reaction methods could be applied to other reactions.

The stage length is designed to allow near complete (>75%, particularly >90%, more so >95% and even more >99%) conversion of oxygen fed in that particular stage. Hence, catalyst loading in the reactor (stage) will also influence the stage length. A varying degree of completeness of oxygen conversion may also be acceptable upon the overall methanol conversion at that reactor location. However, observing the high selectivity of CO formation at ultra low oxygen levels, a design constraint of 0.1% $O_2$ at each stage exit was required in the model.

It is anticipated that mixing features may be needed between oxygen stages to assist with the mixing of the oxidant and the reaction mixture at each stage. In one embodiment the use of a jet or other higher velocity oxidant inlet (velocity of inlet oxidant stream higher than velocity of second feed stream) approach may be sufficient to mix the reaction within the catalyst or before the catalyst and or between catalysts. Surface features, posts, or other mixing features may be needed to mix the two streams near the inlet to each oxidant feed point.

Figure 15:
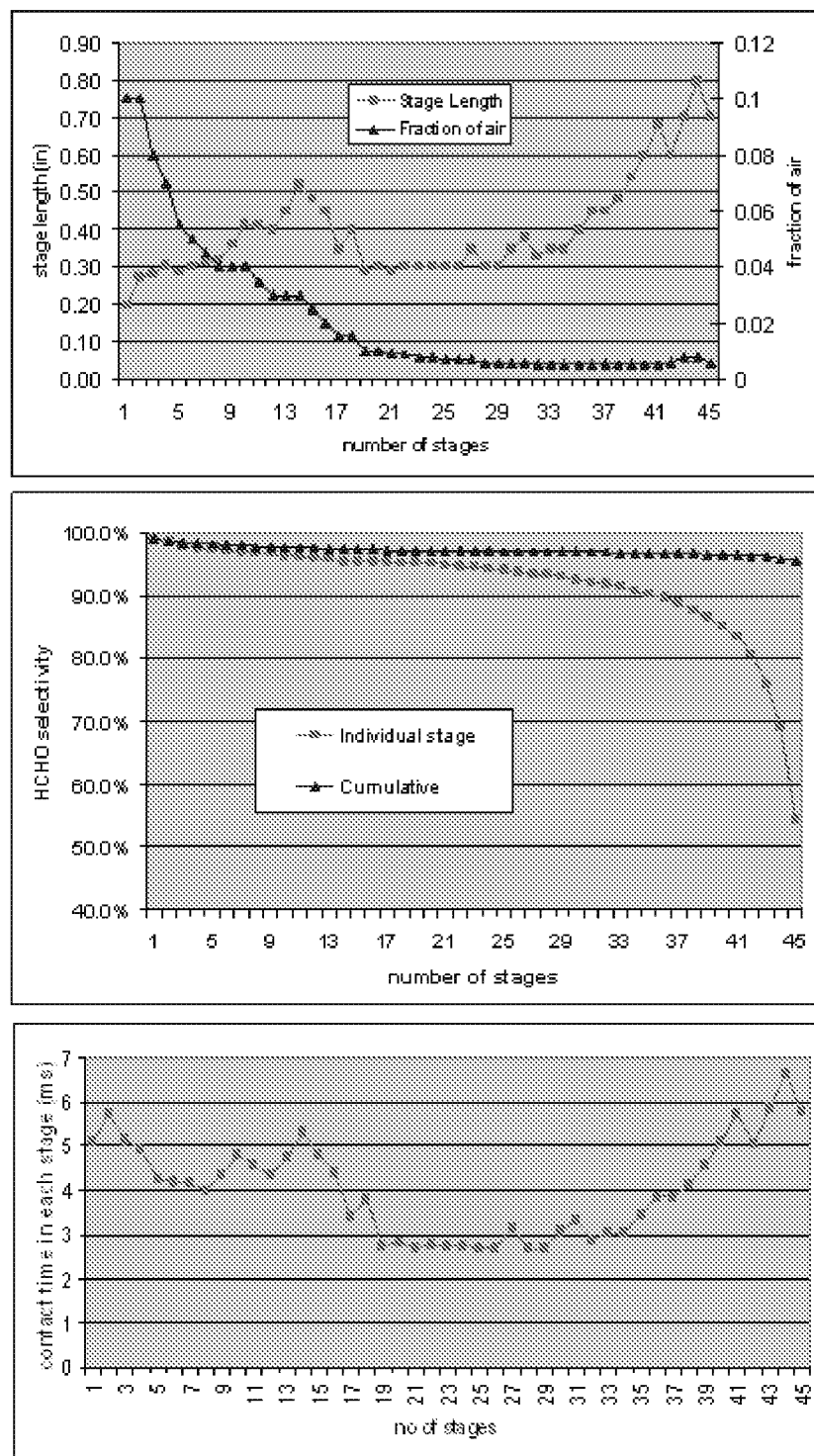
FIG. 15 shows operation conditions and calculated results for operation of a staged reactor at 420° C., with 45 stages, the illustrated air fraction and contact time.
Figure 16:
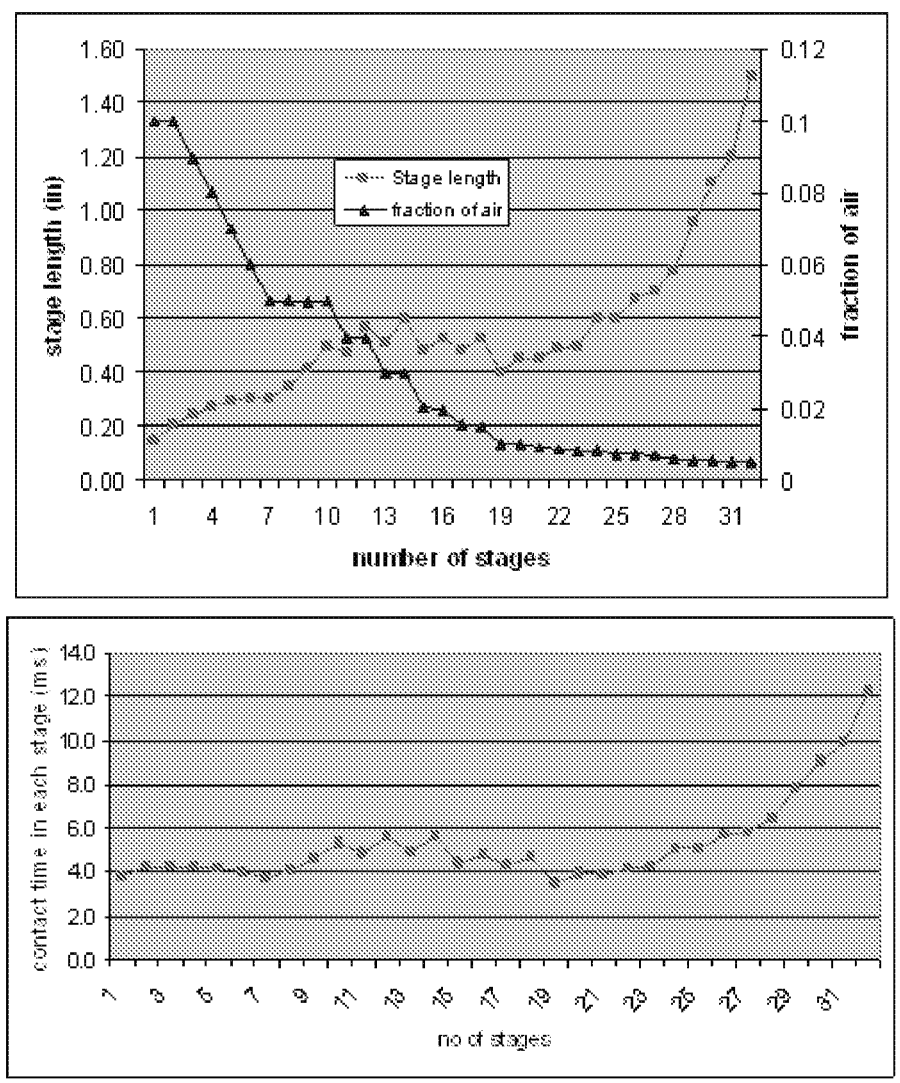
FIG. 16 shows operation conditions and calculated results for operation of a staged reactor at 435° C. with 32 stages.

As proof of concept demonstration, a uniform temperature and uniform catalyst loading per unit length of the reactor was assumed throughout the reactor. Length of each stage and the fraction of air (oxygen) fed into the reactor were used as the primary tuning variables and these vary with each stage (see FIGS. 15a and 16a).

Unequal Feed Fraction of Air (Oxygen):

Shorter stages with larger air fractions are used near the inlet of the reactor. These stages help achieve high selectivity at modest conversion (up to 10%) of methanol and near complete conversion of oxygen (>95%). The intermediate stages were aimed at achieving the maximum selectivity even at the cost of slightly lower conversions. The last few stages in the reactor are longer stages (with low feed fraction of air) that are designed to achieve high reactant (methanol) conversion even at the cost of lower formaldehyde selectivity (see FIG. 15b).

Unequal Stages Length:

Overall, nearly monotonic increase in the stage length (of the form $Ae^{Bn}$, n=no. of stages) and decrease in the fraction of air fed (of the form $A(1-e^{Bn})$) are seen over the reactor stage length. The methanol conversion achieved in the reactor approximately equals the total amount of air introduced (to that point) since the cumulative oxygen conversion in the reactor is >99% along the entire reactor length.

Also contemplated is an operating strategy where the contact time in each stage could be held constant and stage length increased progressively to accommodate for the higher flow rate in each subsequent stage. Alternately, if the loss products due to slower reactions dominate, then one could have stages with decreasing contact times. However, one would need to be careful about the impact on selectivity and yield while implementing these approaches as the reaction kinetics will also play a significant role.

Figure 17:
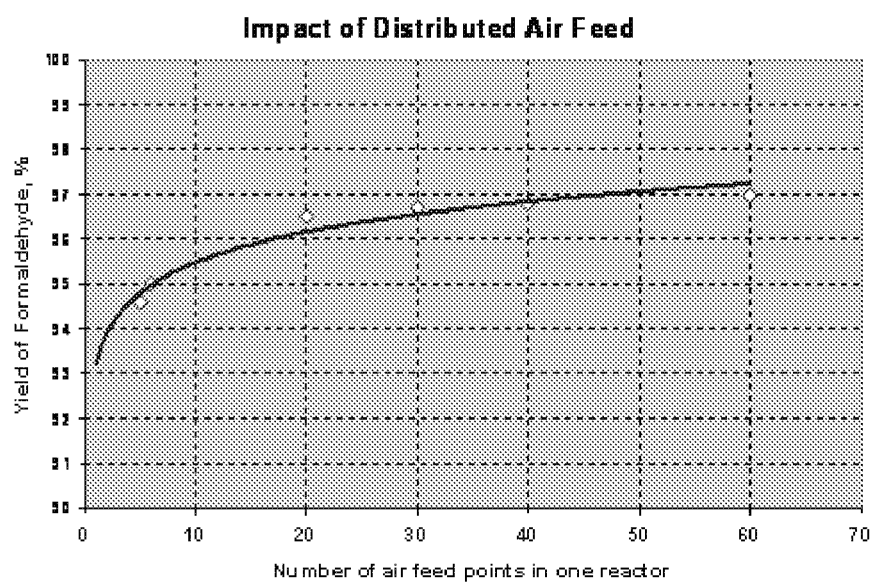
FIG. 17 shows that by controlling oxygen fed in plural stages overall HCHO yield can be increased.

Using these strategies, reactor simulations with increasing number of stages (but fixed temperature and catalyst loading per unit length) were performed. Increasing yields (94.6 to 97%) are seen with increase in the number of stages for air feed (5-60) as is shown in FIG. 17, highlighting the success of the approach described above.

What is claimed:

1. Microchannel apparatus, comprising:
   a bulk flow path having at least one dimension of 2 mm or less;
   a channel wall adjacent to the bulk flow path;
   wherein the channel wall comprises a well with sloped walls and a mesoporous matrix material disposed in the well; and
   wherein the mesoporous matrix is confined in the well and does not coat walls of the bulk flow path outside the well.

2. The microchannel apparatus of claim 1 further comprising a catalyst, which is not disposed on a mesoporous matrix, disposed on walls around the bulk flow path that is not within a well.

3. The microchannel apparatus of claim 1 wherein the mesoporous matrix comprises a structured wall and wherein the structured wall is made of layers forming a stair-step design.

4. The microchannel apparatus of claim 1 wherein the well is sloped from a direction of flow at an angle of taper of from 30° to 60°.

5. The microchannel apparatus of claim 3 comprising at least 5 steps.

6. The microchannel apparatus of claim 3 comprising 3 to 30 steps.

7. The microchannel apparatus of claim 1 wherein the channel wall is cylindrical and the sloped wall is formed by cylindrical mesh sleeves.

8. The microchannel apparatus of claim 1 wherein the well is sloped from a direction of flow at an angle of taper of from 20° to 70°.

9. The microchannel apparatus of claim 1 wherein the mesoporous matrix comprises a structured wall.

10. The microchannel apparatus of claim 1 wherein the mesoporous matrix comprises a large pore support wherein at least 50% of the large pore support's pore volume is composed of pores in the size range of 0.3 to 200 μm.

* * * * *